United States Patent
Lu et al.

(10) Patent No.: US 9,675,687 B2
(45) Date of Patent: Jun. 13, 2017

(54) COMPOSITIONS AND METHODS TO TREAT AIDS

(71) Applicant: University of Massachusetts, Boston, MA (US)

(72) Inventors: Shan Lu, Hopkinton, MA (US); Shixia Wang, Northborough, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 14/776,682

(22) PCT Filed: Mar. 13, 2014

(86) PCT No.: PCT/US2014/026247
§ 371 (c)(1),
(2) Date: Sep. 14, 2015

(87) PCT Pub. No.: WO2014/151687
PCT Pub. Date: Sep. 25, 2014

(65) Prior Publication Data
US 2016/0015802 A1    Jan. 21, 2016

Related U.S. Application Data

(60) Provisional application No. 61/788,837, filed on Mar. 15, 2013.

(51) Int. Cl.
```
A61K 39/21      (2006.01)
A61K 39/12      (2006.01)
A61K 45/06      (2006.01)
C07K 14/005     (2006.01)
C12N 7/00       (2006.01)
A61K 39/00      (2006.01)
```

(52) U.S. Cl.
CPC .............. *A61K 39/21* (2013.01); *A61K 39/12* (2013.01); *A61K 45/06* (2013.01); *C07K 14/005* (2013.01);
(Continued)

(58) Field of Classification Search
None
See application file for complete search history.

(56) References Cited

U.S. PATENT DOCUMENTS

2007/0178562 A1    8/2007  Haynes
2008/0274134 A1*  11/2008  Schulke ................. A61K 39/21
                                                   424/196.11
(Continued)

FOREIGN PATENT DOCUMENTS

WO    WO 2004050856 A2 *  6/2004 ............. A61K 39/21
WO    WO2005027840 A2      3/2005
WO    WO 2005028625 A2 *  3/2005 ............. A61K 39/21

OTHER PUBLICATIONS

Gao et al. "Molecular Cloning and Analysis of Functional Envelope Genes from Human Immunodeficiency Virus Type 1 Sequence Subtypes A through G," Journal of Virology, vol. 79, No. 3: 1651-1667 (1996).*

(Continued)

*Primary Examiner* — Janet L Andres
*Assistant Examiner* — M. Franco Salvoza
(74) *Attorney, Agent, or Firm* — Fish & Richardson P.C.

(57) ABSTRACT

Polyvalent, primary isolate nucleic acid compositions for inducing an immune response against HIV are disclosed. The compositions and methods described herein are for the use of a nucleic acid composition that encodes one or more different HIV envelope glycoproteins. The synthetic, codon-optimized DNAs encoding one or more HIV proteins are a combination of different nucleic acids, such as DNA plasmids, generated from primary isolate DNA of different HIV major group genetic clades and/or different proteins. HIV polypeptide compositions for inducing an immune response against HIV are also disclosed. Methods for using the
(Continued)

polypeptide compositions before, at the same time as, and/or after administration of the DNA compositions are provided.

21 Claims, 5 Drawing Sheets

(52) U.S. Cl.
CPC ............ *C12N 7/00* (2013.01); *A61K 2039/53* (2013.01); *A61K 2039/54* (2013.01); *A61K 2039/545* (2013.01); *A61K 2039/575* (2013.01); *A61K 2039/70* (2013.01); *C12N 2740/16134* (2013.01)

(56) References Cited

U.S. PATENT DOCUMENTS

2009/0175910 A1   7/2009  Nabel
2011/0262488 A1   10/2011 Phogat

OTHER PUBLICATIONS

Pal, R. et al, "Immunization of rhesus macaques with a polyvalent DNA prime/protein boost human immunodeficiency virus type 1 vaccine elicits protective antibody response against simian human immunodeficiency virus of R5 phenotype," Virology, vol. 348:341-353 (2006).
Wang, S. et al., "Cross-subtype antibody and cellular immune responses induced by a polyvalent DNA prime-protein boost HIV-1 vaccine in healthy human volunteers," Vaccine, vol. 26:3947-3957 (2008).
Wang, S, et al., "Polyvalent HIV-1 Env vaccine formulations delivered by the DNA priming plus protein boosting approach are effective in generating neutralizing antibodies against primary human immunodeficiency virus type 1 isolates from subtypes A, B, C, D and E," Virology, vol. 350:34-47 (2006).
Notification of Transmittal of the International Search Report and the Written Opinion of the International searching Authority for PCT PCT/US 14/26247, mailed Apr. 2, 2015, 14 pages.

* cited by examiner

SEQUENCE LISTING

<160> NUMBER OF SEQ ID NOS: 16

<210> SEQ ID NO 1
<211> LENGTH: 1410
<212> TYPE: DNA
<213> ORGANISM: Artificial Sequence
<220> FEATURE:
<223> OTHER INFORMATION: laboratory-synthesized sequences

<400> SEQUENCE: 1

```
ctgtgggtga ccgtgtacta cggcgtgccc gtgtggaagg acgccgagac caccctgttc      60
tgcgccagcg acgccaaggc ctacgacacc gaggtgcaca acgtgtgggc cacccacgcc     120
tgcgtgccca ccgaccccaa cccccaggag atctacatgg agaacgtgac cgaggagttc     180
aacatgtgga agaacaacat ggtggagcag atgcacaccg acatcatcag cctgtgggac     240
cagagcctga agccctgcgt gcagctgacc cccctgtgcg tgaccctgga ctgcagctac     300
aacatcacca caacatcac caacagcatc accaacagca gcgtgaacat gcgcgaggag     360
atcaagaact gcagcttcaa catgaccacc gagctgcgcg acaagaaccg caaggtgtac     420
agcctgttct acaagctgga cgtggtgcag atcaacaacg gcaacaacag cagcaacctg     480
taccgcctga tcaactgcaa caccagcgcc ctgacccagg cctgccccaa ggtgaccttc     540
gagcccatcc ccatccgcta ctgcgccccc gccggctacg ccatcctgaa gtgcaacgac     600
aaggagttca acggcaccgg cctgtgcaag aacgtgagca ccgtgcagtg cacccacggc     660
atccgccccg tggtgagcac ccagctgctg ctgaacggca gcctggccga gggcaaggtg     720
atgatccgca gcgagaacat caccaacaac gtgaagaaca tcatcgtgca gctgaacgag     780
accgtgacca tcaactgcac ccgccccaac aacaacaccc gcaagagcgt gcgcatcggc     840
cccggccaga ccttctacgc caccggcgac atcatcggcg acatccgcca ggcccactgc     900
aacgtgagcg cagccagtg gaaccgcgcc ctgcaccagg tggtgggcca gctgcgcgag     960
tactggaaca ccaccatcat cttcaagaac agcagcggcg gcgacctgga gatcaccacc    1020
cacagcttca actgcggcgg cgagttcttc tactgcaaca ccagcggcct gttcaacagc    1080
aactggaccc acaacgacac cgccagcatg aagcccaacg acaccatcac cctgccctgc    1140
cgcatcaagc agatcatcaa catgtggcag cgcgtgggcc aggccatcta cgcccctccc    1200
atccagggcg tgatccgctg cgagagcaac atcaccggcc tgatcctgac ccgcgacggc    1260
ggcggcaaca tcaacgagag ccagatcttc cgccccggcg cggcgacat gcgcgacaac    1320
tggcgcagcg agctgtacaa gtacaaggtg gtgcgcatcg agcccctggg cgtggccccc    1380
accaaggcca gcgccgcgt ggtggagtaa                                      1410
```

<210> SEQ ID NO 2
<211> LENGTH: 469
<212> TYPE: PRT
<213> ORGANISM: Artificial Sequence
<220> FEATURE:
<223> OTHER INFORMATION: laboratory-synthesized sequences

<400> SEQUENCE: 2

```
Leu Trp Val Thr Val Tyr Tyr Gly Val Pro Val Trp Lys Asp Ala Glu
 1               5                  10                  15

Thr Thr Leu Phe Cys Ala Ser Asp Ala Lys Ala Tyr Asp Thr Glu Val
             20                  25                  30

His Asn Val Trp Ala Thr His Ala Cys Val Pro Thr Asp Pro Asn Pro
         35                  40                  45
```

-continued

```
Gln Glu Ile Tyr Met Glu Asn Val Thr Glu Glu Phe Asn Met Trp Lys
        50                  55                  60

Asn Asn Met Val Glu Gln Met His Thr Asp Ile Ile Ser Leu Trp Asp
 65                  70                  75                  80

Gln Ser Leu Lys Pro Cys Val Gln Leu Thr Pro Leu Cys Val Thr Leu
                 85                  90                  95

Asp Cys Ser Tyr Asn Ile Thr Asn Asn Ile Thr Asn Ser Ile Thr Asn
                100                 105                 110

Ser Ser Val Asn Met Arg Glu Glu Ile Lys Asn Cys Ser Phe Asn Met
             115                 120                 125

Thr Thr Glu Leu Arg Asp Lys Asn Arg Lys Val Tyr Ser Leu Phe Tyr
         130                 135                 140

Lys Leu Asp Val Val Gln Ile Asn Asn Gly Asn Asn Ser Ser Asn Leu
145                 150                 155                 160

Tyr Arg Leu Ile Asn Cys Asn Thr Ser Ala Leu Thr Gln Ala Cys Pro
                 165                 170                 175

Lys Val Thr Phe Glu Pro Ile Pro Ile Arg Tyr Cys Ala Pro Ala Gly
             180                 185                 190

Tyr Ala Ile Leu Lys Cys Asn Asp Lys Glu Phe Asn Gly Thr Gly Leu
         195                 200                 205

Cys Lys Asn Val Ser Thr Val Gln Cys Thr His Gly Ile Arg Pro Val
210                 215                 220

Val Ser Thr Gln Leu Leu Leu Asn Gly Ser Leu Ala Glu Gly Lys Val
225                 230                 235                 240

Met Ile Arg Ser Glu Asn Ile Thr Asn Asn Val Lys Asn Ile Ile Val
                 245                 250                 255

Gln Leu Asn Glu Thr Val Thr Ile Asn Cys Thr Arg Pro Asn Asn Asn
             260                 265                 270

Thr Arg Lys Ser Val Arg Ile Gly Pro Gly Gln Thr Phe Tyr Ala Thr
         275                 280                 285

Gly Asp Ile Ile Gly Asp Ile Arg Gln Ala His Cys Asn Val Ser Gly
    290                 295                 300

Ser Gln Trp Asn Arg Ala Leu His Gln Val Val Gly Gln Leu Arg Glu
305                 310                 315                 320

Tyr Trp Asn Thr Thr Ile Ile Phe Lys Asn Ser Ser Gly Gly Asp Leu
                 325                 330                 335

Glu Ile Thr Thr His Ser Phe Asn Cys Gly Gly Glu Phe Phe Tyr Cys
             340                 345                 350

Asn Thr Ser Gly Leu Phe Asn Ser Asn Trp Thr His Asn Asp Thr Ala
         355                 360                 365

Ser Met Lys Pro Asn Asp Thr Ile Thr Leu Pro Cys Arg Ile Lys Gln
    370                 375                 380

Ile Ile Asn Met Trp Gln Arg Val Gly Gln Ala Ile Tyr Ala Pro Pro
385                 390                 395                 400

Ile Gln Gly Val Ile Arg Cys Glu Ser Asn Ile Thr Gly Leu Ile Leu
                 405                 410                 415

Thr Arg Asp Gly Gly Asn Ile Asn Glu Ser Gln Ile Phe Arg Pro
             420                 425                 430

Gly Gly Gly Asp Met Arg Asp Asn Trp Arg Ser Glu Leu Tyr Lys Tyr
         435                 440                 445

Lys Val Val Arg Ile Glu Pro Leu Gly Val Ala Pro Thr Lys Ala Lys
450                 455                 460

Arg Arg Val Val Glu
```

<210> SEQ ID NO 3
<211> LENGTH: 1428
<212> TYPE: DNA
<213> ORGANISM: Artificial Sequence
<220> FEATURE:
<223> OTHER INFORMATION: laboratory-synthesized sequences

<400> SEQUENCE: 3

```
gtggagaagc tgtgggtgac tgtatactat ggggtgcctg tgtggaagga ggccaccacc      60
accctgttct gtgcctctga tgccaaggcc tatgacactg aggtccacaa tgtctgggcc     120
acccatgcct gtgtgcccac tgaccccaac cctcaggagg tggtgctgga gaatgtgact     180
gagcacttca acatgtggaa gaacaacatg gtggagcaga tgcaggagga catcatcagc     240
ctgtgggacc agagcctgaa gccctgtgtg aagctgaccc ccctgtgtgt gaccctgaac     300
tgcaaggatg tgaatgccac caacaccacc aatgactctg agggcactat ggagaggggt     360
gagatcaaga actgcagctt caacatcacc accagcatca gggatgaggt gcagaaggag     420
tatgccctgt tctacaagct ggatgtggtg cccattgaca caacaacac cagctacagg      480
ctgatcagct gtgacacctc tgtgatcacc caggcctgcc ccaagatcag ctttgagccc     540
atccccatcc actactgtgc ccctgctggc tttgccatcc tgaagtgcaa tgacaagacc     600
ttcaatggca aaggcccttg caagaatgtg agcactgtgc agtgcactca tggcatcagg     660
cctgtggtga gcacccagct gctgctgaat ggcagcctgg ctgaggagga ggtggtgatc     720
aggtctgaca acttcaccaa caatgccaag accatcattg tgcagctgaa ggagtctgtg     780
gagatcaact gcaccaggcc caacaacaac accaggaaga gcattcacat tggccctggc     840
agggccttct acaccactgg ggagatcatt ggggacatca gcaggcccca ctgcaacatc     900
agcagggcca gtggaatga cccctgaag cagattgtga tcaagctgag ggagcagttt     960
gagaacaaga ccattgtgtt caatcacagc tctggtggtg atcctgagat tgtgatgcac    1020
agcttcaact gtggtggtga gttcttctac tgcaacagca cccagctgtt caacagcacc    1080
tggaacaaca cactgaggg cagcaacaac actgagggca caccatcac cctgccttgc    1140
aggatcaagc agatcatcaa catgtggcag gaggtgggca aggccatgta tgctcctccc    1200
atcaggggcc agatcaggtg cagcagcaac atcactggcc tgctgctgac agggatggt    1260
ggcatcaatg agaatggcac tgagattttc aggcctggtg gtgggacat gagggacaac    1320
tggaggtctg agctgtacaa gtacaaggtg gtgaagattg agccccttgg tgtggctccc    1380
accaaggcta agcgcagggt ggtgcagagg gagaagcgcg ctgtgtaa              1428
```

<210> SEQ ID NO 4
<211> LENGTH: 475
<212> TYPE: PRT
<213> ORGANISM: Artificial Sequence
<220> FEATURE:
<223> OTHER INFORMATION: laboratory-synthesized sequences

<400> SEQUENCE: 4

```
Val Glu Lys Leu Trp Val Thr Val Tyr Tyr Gly Val Pro Val Trp Lys
  1               5                  10                  15

Glu Ala Thr Thr Thr Leu Phe Cys Ala Ser Asp Ala Lys Ala Tyr Asp
                 20                  25                  30

Thr Glu Val His Asn Val Trp Ala Thr His Ala Cys Val Pro Thr Asp
             35                  40                  45
```

```
Pro Asn Pro Gln Glu Val Val Leu Glu Asn Val Thr Glu His Phe Asn
    50              55                  60
Met Trp Lys Asn Asn Met Val Glu Gln Met Gln Glu Asp Ile Ile Ser
65              70                  75                  80
Leu Trp Asp Gln Ser Leu Lys Pro Cys Val Lys Leu Thr Pro Leu Cys
                85                  90                  95
Val Thr Leu Asn Cys Lys Asp Val Asn Ala Thr Asn Thr Thr Asn Asp
                100                 105                 110
Ser Glu Gly Thr Met Glu Arg Gly Glu Ile Lys Asn Cys Ser Phe Asn
            115                 120                 125
Ile Thr Thr Ser Ile Arg Asp Glu Val Gln Lys Glu Tyr Ala Leu Phe
    130                 135                 140
Tyr Lys Leu Asp Val Val Pro Ile Asp Asn Asn Asn Thr Ser Tyr Arg
145                 150                 155                 160
Leu Ile Ser Cys Asp Thr Ser Val Ile Thr Gln Ala Cys Pro Lys Ile
                165                 170                 175
Ser Phe Glu Pro Ile Pro Ile His Tyr Cys Ala Pro Ala Gly Phe Ala
            180                 185                 190
Ile Leu Lys Cys Asn Asp Lys Thr Phe Asn Gly Lys Gly Pro Cys Lys
    195                 200                 205
Asn Val Ser Thr Val Gln Cys Thr His Gly Ile Arg Pro Val Val Ser
210                 215                 220
Thr Gln Leu Leu Leu Asn Gly Ser Leu Ala Glu Glu Val Val Ile
225                 230                 235                 240
Arg Ser Asp Asn Phe Thr Asn Asn Ala Lys Thr Ile Ile Val Gln Leu
                245                 250                 255
Lys Glu Ser Val Glu Ile Asn Cys Thr Arg Pro Asn Asn Asn Thr Arg
            260                 265                 270
Lys Ser Ile His Ile Gly Pro Gly Arg Ala Phe Tyr Thr Thr Gly Glu
    275                 280                 285
Ile Ile Gly Asp Ile Arg Gln Ala His Cys Asn Ile Ser Arg Ala Lys
290                 295                 300
Trp Asn Asp Thr Leu Lys Gln Ile Val Ile Lys Leu Arg Glu Gln Phe
305                 310                 315                 320
Glu Asn Lys Thr Ile Val Phe Asn His Ser Ser Gly Gly Asp Pro Glu
                325                 330                 335
Ile Val Met His Ser Phe Asn Cys Gly Gly Glu Phe Phe Tyr Cys Asn
            340                 345                 350
Ser Thr Gln Leu Phe Asn Ser Thr Trp Asn Asn Asn Thr Glu Gly Ser
    355                 360                 365
Asn Asn Thr Glu Gly Asn Thr Ile Thr Leu Pro Cys Arg Ile Lys Gln
370                 375                 380
Ile Ile Asn Met Trp Gln Glu Val Gly Lys Ala Met Tyr Ala Pro Pro
385                 390                 395                 400
Ile Arg Gly Gln Ile Arg Cys Ser Ser Asn Ile Thr Gly Leu Leu Leu
                405                 410                 415
Thr Arg Asp Gly Gly Ile Asn Glu Asn Gly Thr Glu Ile Phe Arg Pro
            420                 425                 430
Gly Gly Gly Asp Met Arg Asp Asn Trp Arg Ser Glu Leu Tyr Lys Tyr
    435                 440                 445
Lys Val Val Lys Ile Glu Pro Leu Gly Val Ala Pro Thr Lys Ala Lys
450                 455                 460

Arg Arg Val Val Gln Arg Glu Lys Arg Ala Val
```

<210> SEQ ID NO 5
<211> LENGTH: 1398
<212> TYPE: DNA
<213> ORGANISM: Artificial Sequence
<220> FEATURE:
<223> OTHER INFORMATION: laboratory-synthesized sequences

<400> SEQUENCE: 5

```
ctgtgggtga ccgtgtacta cggcgtgccc gtgtggaagg aggccaagac caccctgttc      60
tgcgccagcg aggccaaggc ctacgagaag gaggtgcaca acgtgtgggc cacccacgcc     120
tgcgtgccca ccgaccccaa cccccaggag atggtgctgg agaacgtgac cgagaacttc     180
aacatgtgga gaacgacat ggtgaaccag atgcacgagg acatcatcag cctgtgggac     240
cagagcctga agccctgcgt gaagctgacc cccctgtgcg tgaccctgaa ctgcaccaac     300
gccaacggca ccaacaataa cggcaccgtg aacgtgaacg acaccatgta cggcgagatc     360
aagaactgca gcttcaacat gaccaccgag ctgcgggaca gaagaagca ggtgtacgcc      420
ctgttctaca agctggacat cgtgagcctg aacgagaaca gcaacaacag cagcgagtac     480
cggctgatca actgcaacac cagcgtgatc acccaggcct gccccaaggt gaccttcgac     540
cccatcccca tccactactg cgcccctgcc ggctacgcca tcctgaagtg caacaacaag     600
accttcaccg gcatcggccc ctgcaagaac gtgagcaccg tgcagtgcac ccacggcatc     660
aagcccgtgg tgagcaccca gctgctgctg aacggcagcc tggccgagga ggagatcatc     720
gtgcggagcg agaacctgac cgacaacgtg aaaaccatca tcgtgcacct gaatgagagc     780
gtggagatcg tgtgcaccag gcccaacaac aacacccgga gagcgtgcg gatcggccct     840
ggccagacct tctacgccac cggcgccatc atcggcgaca tccggcaggc ccactgcaac     900
atcagcacca tcaagtggaa caagaccctg cagggcgtgg agaagaagct gaaggagcac     960
ttcccccaaca gaccatcga gttcaagccc agcagcggcg agacctgga gatcaccacc    1020
cacagcttca actgcagggg cgagttcttc tgctgcaaca cctccaacct gttcaccagc    1080
aatctgttca ccgacaacct gaccaacacc accaacatca ccctgccctg ccggatcaag    1140
cagatcatca acatgtggca gggcgtgggc agggccatgt acgcccctcc catcgccggc    1200
aacatcacct gcaagagcaa catcaccggc ctgctgctga cccgggacgg cggcgagaac    1260
aaccggaccg agaccttcag gcccggaggc ggcgacatga aggacaactg gcggagcgag    1320
ctgtacaagt acaaggtggt ggagatcaag cccctgggcg tggcccccac cggcgccaag    1380
cgccgcgtgg tggagtaa                                                  1398
```

<210> SEQ ID NO 6
<211> LENGTH: 465
<212> TYPE: PRT
<213> ORGANISM: Artificial Sequence
<220> FEATURE:
<223> OTHER INFORMATION: laboratory-synthesized sequences

<400> SEQUENCE: 6

```
Leu Trp Val Thr Val Tyr Tyr Gly Val Pro Val Trp Lys Glu Ala Lys
  1               5                  10                  15

Thr Thr Leu Phe Cys Ala Ser Glu Ala Lys Ala Tyr Glu Lys Glu Val
             20                  25                  30

His Asn Val Trp Ala Thr His Ala Cys Val Pro Thr Asp Pro Asn Pro
         35                  40                  45
```

-continued

Gln Glu Met Val Leu Glu Asn Val Thr Glu Asn Phe Asn Met Trp Lys
 50                  55                  60

Asn Asp Met Val Asn Gln Met His Glu Asp Ile Ile Ser Leu Trp Asp
 65                  70                  75                  80

Gln Ser Leu Lys Pro Cys Val Lys Leu Thr Pro Leu Cys Val Thr Leu
                 85                  90                  95

Asn Cys Thr Asn Ala Asn Gly Thr Asn Asn Gly Thr Val Asn Val
             100                 105                 110

Asn Asp Thr Met Tyr Gly Glu Ile Lys Asn Cys Ser Phe Asn Met Thr
             115                 120                 125

Thr Glu Leu Arg Asp Lys Lys Gln Val Tyr Ala Leu Phe Tyr Lys
         130                 135                 140

Leu Asp Ile Val Ser Leu Asn Glu Asn Ser Asn Ser Ser Glu Tyr
145                 150                 155                 160

Arg Leu Ile Asn Cys Asn Thr Ser Val Ile Thr Gln Ala Cys Pro Lys
                 165                 170                 175

Val Thr Phe Asp Pro Ile Pro Ile His Tyr Cys Ala Pro Ala Gly Tyr
             180                 185                 190

Ala Ile Leu Lys Cys Asn Asn Lys Thr Phe Thr Gly Ile Gly Pro Cys
         195                 200                 205

Lys Asn Val Ser Thr Val Gln Cys Thr His Gly Ile Lys Pro Val Val
210                 215                 220

Ser Thr Gln Leu Leu Leu Asn Gly Ser Leu Ala Glu Glu Ile Ile
225                 230                 235                 240

Val Arg Ser Glu Asn Leu Thr Asp Asn Val Lys Thr Ile Ile Val His
                 245                 250                 255

Leu Asn Glu Ser Val Glu Ile Val Cys Thr Arg Pro Asn Asn Asn Thr
             260                 265                 270

Arg Lys Ser Val Arg Ile Gly Pro Gly Gln Thr Phe Tyr Ala Thr Gly
         275                 280                 285

Ala Ile Ile Gly Asp Ile Arg Gln Ala His Cys Asn Ile Ser Thr Ile
290                 295                 300

Lys Trp Asn Lys Thr Leu Gln Gly Val Glu Lys Lys Leu Lys Glu His
305                 310                 315                 320

Phe Pro Asn Lys Thr Ile Glu Phe Lys Pro Ser Ser Gly Gly Asp Leu
                 325                 330                 335

Glu Ile Thr Thr His Ser Phe Asn Cys Arg Gly Glu Phe Phe Cys Cys
             340                 345                 350

Asn Thr Ser Asn Leu Phe Thr Ser Asn Leu Phe Thr Asp Asn Leu Thr
         355                 360                 365

Asn Thr Thr Asn Ile Thr Leu Pro Cys Arg Ile Lys Gln Ile Ile Asn
370                 375                 380

Met Trp Gln Gly Val Gly Arg Ala Met Tyr Ala Pro Pro Ile Ala Gly
385                 390                 395                 400

Asn Ile Thr Cys Lys Ser Asn Ile Thr Gly Leu Leu Leu Thr Arg Asp
                 405                 410                 415

Gly Gly Glu Asn Asn Arg Thr Glu Thr Phe Arg Pro Gly Gly Gly Asp
             420                 425                 430

Met Lys Asp Asn Trp Arg Ser Glu Leu Tyr Lys Tyr Lys Val Val Glu
         435                 440                 445

Ile Lys Pro Leu Gly Val Ala Pro Thr Gly Ala Lys Arg Arg Val Val
450                 455                 460

Glu

-continued

<210> SEQ ID NO 7
<211> LENGTH: 1383
<212> TYPE: DNA
<213> ORGANISM: Artificial Sequence
<220> FEATURE:
<223> OTHER INFORMATION: laboratory-synthesized sequences

<400> SEQUENCE: 7

```
ctgtgggtga ccgtgtacta cggcgtgccc gtgtggaagg aggccaccac cacccctgttc      60
tgcgccagcg acgccaagag ctacgaggcc gaggcccaca acatctgggc cacccacgcc     120
tgcgtgccca ccgaccccaa ccccccaggag atcgtgctgg agaacgtgac cgagaacttc     180
aacatctgga gaacaacat ggtggagcag atgcacgacg acatcatcag cctgtgggac      240
cagagcatca agccctgcgt gaagctgacc ccctgtgcg tgaccctgaa ctgcaccgag       300
tggaagaacg ccaccacaaa cgccaccaac gagggcatcg gcatgaagaa ctgcagcttc     360
accgaggtgc gggacaagaa gaagcaggcc tacgccctgt tctacaagct ggacgtggtg     420
cagatgaacg acgataacag caccaacacc agctaccggc tgatcaactg caacgccagc     480
accatcaccc aggcctgccc caagatcagc ttcgagccca tccccatcca ctactgcgcc     540
cctgccggct cgccatcct gaagtgcaac gacaagaagt caacggcac cggcccctgc       600
aagaacgtga gcaccgtgca gtgcacccac ggcatcaagc ccgtggtgag cacccagctg     660
ctgctgaacg gcagcctggc cgaggaggag atcatcatcc ggagcaagaa cctgaccaac     720
aacgccaaga tcatcatcgt gcacctgaac gagagcgtgc ccatcaactg caccggccc       780
tacgacaagg tgagctaccg gaccccatc ggcgtgggca gggccagcta caccacccgg      840
atcaaggcg acatccggca ggcccactgc aacatcagcg cgagaagtg gaacaagacc       900
ctgcagcagg tggccgtgaa gctgcgggac ctgctgaacc agaccgccat catcttcaag     960
cccagcagcg gcgagaccc cgagatcacc acccacagct tcaactgtgg cggcgagttc    1020
ttctactgca caccagcgg cctgttcaac aacagcgtgt ggaccagcaa cagcaccatc    1080
ggcgccaacg gcaccatcac cctgccctgc aggatcaagc agatcatcaa catgtggcag    1140
ggcgtgggca aggccatgta cgcccctccc atcgagggcc agatcaactg cagctccacc    1200
atcaccggcc tgctgctgac ccgggacggc ggcgtgaaga caacagcca gaacgagacc    1260
ttcaggcccg gaggcggcga catgcgggac aactggcgga cgagctgta caagtacaag    1320
gtggtgcgga tcgagcccct gggcctggcc cccaccaagg ccaagcgccg cgtggtggag    1380
taa                                                                  1383
```

<210> SEQ ID NO 8
<211> LENGTH: 460
<212> TYPE: PRT
<213> ORGANISM: Artificial Sequence
<220> FEATURE:
<223> OTHER INFORMATION: laboratory-synthesized sequences

<400> SEQUENCE: 8

```
Leu Trp Val Thr Val Tyr Tyr Gly Val Pro Val Trp Lys Glu Ala Thr
 1               5                  10                  15

Thr Thr Leu Phe Cys Ala Ser Asp Ala Lys Ser Tyr Glu Ala Glu Ala
            20                  25                  30

His Asn Ile Trp Ala Thr His Ala Cys Val Pro Thr Asp Pro Asn Pro
        35                  40                  45
```

```
Gln Glu Ile Val Leu Glu Asn Val Thr Glu Asn Phe Asn Ile Trp Lys
 50                  55                  60

Asn Asn Met Val Glu Gln Met His Asp Asp Ile Ile Ser Leu Trp Asp
 65                  70                  75                  80

Gln Ser Ile Lys Pro Cys Val Lys Leu Thr Pro Leu Cys Val Thr Leu
                 85                  90                  95

Asn Cys Thr Glu Trp Lys Asn Ala Thr Thr Asn Ala Thr Asn Glu Gly
            100                 105                 110

Ile Gly Met Lys Asn Cys Ser Phe Thr Glu Val Arg Asp Lys Lys Lys
            115                 120                 125

Gln Ala Tyr Ala Leu Phe Tyr Lys Leu Asp Val Val Gln Met Asn Asp
130                 135                 140

Asp Asn Ser Thr Asn Thr Ser Tyr Arg Leu Ile Asn Cys Asn Ala Ser
145                 150                 155                 160

Thr Ile Thr Gln Ala Cys Pro Lys Ile Ser Phe Glu Pro Ile Pro Ile
                165                 170                 175

His Tyr Cys Ala Pro Ala Gly Phe Ala Ile Leu Lys Cys Asn Asp Lys
            180                 185                 190

Lys Phe Asn Gly Thr Gly Pro Cys Lys Asn Val Ser Thr Val Gln Cys
            195                 200                 205

Thr His Gly Ile Lys Pro Val Val Ser Thr Gln Leu Leu Leu Asn Gly
            210                 215                 220

Ser Leu Ala Glu Glu Glu Ile Ile Ile Arg Ser Lys Asn Leu Thr Asn
225                 230                 235                 240

Asn Ala Lys Ile Ile Ile Val His Leu Asn Glu Ser Val Pro Ile Asn
                245                 250                 255

Cys Thr Arg Pro Tyr Asp Lys Val Ser Tyr Arg Thr Pro Ile Gly Val
            260                 265                 270

Gly Arg Ala Ser Tyr Thr Thr Arg Ile Lys Gly Asp Ile Arg Gln Ala
            275                 280                 285

His Cys Asn Ile Ser Gly Glu Lys Trp Asn Lys Thr Leu Gln Gln Val
            290                 295                 300

Ala Val Lys Leu Arg Asp Leu Leu Asn Gln Thr Ala Ile Ile Phe Lys
305                 310                 315                 320

Pro Ser Ser Gly Gly Asp Pro Glu Ile Thr Thr His Ser Phe Asn Cys
                325                 330                 335

Gly Gly Glu Phe Phe Tyr Cys Asn Thr Ser Gly Leu Phe Asn Asn Ser
            340                 345                 350

Val Trp Thr Ser Asn Ser Thr Ile Gly Ala Asn Gly Thr Ile Thr Leu
            355                 360                 365

Pro Cys Arg Ile Lys Gln Ile Ile Asn Met Trp Gln Gly Val Gly Lys
            370                 375                 380

Ala Met Tyr Ala Pro Pro Ile Glu Gly Gln Ile Asn Cys Ser Ser Thr
385                 390                 395                 400

Ile Thr Gly Leu Leu Leu Thr Arg Asp Gly Gly Val Lys Asn Asn Ser
                405                 410                 415

Gln Asn Glu Thr Phe Arg Pro Gly Gly Gly Asp Met Arg Asp Asn Trp
            420                 425                 430

Arg Asn Glu Leu Tyr Lys Tyr Lys Val Val Arg Ile Glu Pro Leu Gly
            435                 440                 445

Leu Ala Pro Thr Lys Ala Lys Arg Arg Val Val Glu
450                 455                 460
```

<210> SEQ ID NO 9
<211> LENGTH: 1410
<212> TYPE: DNA
<213> ORGANISM: Artificial Sequence
<220> FEATURE:
<223> OTHER INFORMATION: laboratory-synthesized sequences

<400> SEQUENCE: 9

```
ctgtgggtca ccgtgtacta cggcgtgccc gtgtggcggg acgccgatac caccctgttc      60
tgtgccagcg acgccaaggc ccacgagaca gaggtgcaca acgtgtgggc cacccacgcc     120
tgcgtgccca ccgaccccaa cccccaggaa atccacctgg aaaacgtgac cgagaacttc     180
aacatgtgga gaacaacat ggtcgagcag atgcaggaag atgtcatcag cctctgggac      240
cagagcctga agccctgcgt gaagctgacc cccctgtgcg tgaccctgaa ctgcaccaac     300
gccaacctga ccaacaacaa catcaacggc agcaacatca tcggcaacat caccgacgaa     360
gtgcggaact gctccttcaa catgaccacc gagctgcggg acaagaaaca gaaggtgcac     420
gccctgttct acaagctgga catcgtgcag atcgaggaca cagcaacag cagcgagtac     480
cggctgatca actgcaacac cagcgtgatc aagcaggcct gccccaagat cagcttcgac     540
cccatcccca tccactactg cacccctgcc ggctacgcca tcctgaagtg caacgacaag     600
aacttcaatg gcaccggccc ctgcaagaac gtgtccagcg tgcagtgcac ccacggcatc     660
aagcccgtgg tgtccacccca gctgctgctg aatggcagcc tggccgagga agagatcatc     720
atcagaagcg agaacctcac caacaatgcc aagaccatca tcgtgcacct gaacaagagc     780
gtggaaatca ctgcacccg gcccagcaac aacacccgga ccagcatcac catcggccct     840
ggccaggtgt tctaccggac cggcgatatc atcggcgata tccggaaggc ctactgcgag     900
atcaacggca ccaagtggaa cgaggtgctg aagcaggtca caggcaagct gaaagagcac     960
ttcaacaaca agacaatcat cttccagccc ccctctggcg gcgacctgga aatcaccatg    1020
caccacttca actgtcgggg cgagttcttc tactgcaata ccaccaagct gttcaacaat    1080
acctgcatcg gcaacgagac aatggaaggc tgcaatggca ccatcatcct gccctgcaag    1140
atcaagcaga tcatcaatat gtggcagggc gtgggccagg ctatgtacgc ccctcccatc    1200
agcggccgga tcaactgcgt gtccaatatc accggcatcc tgctgacccg ggacggcgga    1260
gccaacaaca ccgccaacga gacattcaga cccggcggag caacatcaa ggacaactgg    1320
cggagcgagc tgtacaagta caaggtggtg cagattgagc ccctgggaat cgcccccacc    1380
cgggccaagc ggagagtggt ggaatgatga                                    1410
```

<210> SEQ ID NO 10
<211> LENGTH: 468
<212> TYPE: PRT
<213> ORGANISM: Artificial Sequence
<220> FEATURE:
<223> OTHER INFORMATION: laboratory-synthesized sequences

<400> SEQUENCE: 10

```
Leu Trp Val Thr Val Tyr Tyr Gly Val Pro Val Trp Arg Asp Ala Asp
  1               5                  10                  15

Thr Thr Leu Phe Cys Ala Ser Asp Ala Lys Ala His Glu Thr Glu Val
             20                  25                  30

His Asn Val Trp Ala Thr His Ala Cys Val Pro Thr Asp Pro Asn Pro
         35                  40                  45

Gln Glu Ile His Leu Glu Asn Val Thr Glu Asn Phe Asn Met Trp Lys
     50                  55                  60
```

-continued

```
Asn Asn Met Val Glu Gln Met Gln Glu Asp Val Ile Ser Leu Trp Asp
 65                  70                  75                  80

Gln Ser Leu Lys Pro Cys Val Lys Leu Thr Pro Leu Cys Val Thr Leu
                 85                  90                  95

Asn Cys Thr Asn Ala Asn Leu Thr Asn Asn Asn Ile Asn Gly Ser Asn
                100                 105                 110

Ile Ile Gly Asn Ile Thr Asp Glu Val Arg Asn Cys Ser Phe Asn Met
            115                 120                 125

Thr Thr Glu Leu Arg Asp Lys Lys Gln Lys Val His Ala Leu Phe Tyr
130                 135                 140

Lys Leu Asp Ile Val Gln Ile Glu Asp Asn Ser Asn Ser Ser Glu Tyr
145                 150                 155                 160

Arg Leu Ile Asn Cys Asn Thr Ser Val Ile Lys Gln Ala Cys Pro Lys
                165                 170                 175

Ile Ser Phe Asp Pro Ile Pro Ile His Tyr Cys Thr Pro Ala Gly Tyr
            180                 185                 190

Ala Ile Leu Lys Cys Asn Asp Lys Asn Phe Asn Gly Thr Gly Pro Cys
        195                 200                 205

Lys Asn Val Ser Ser Val Gln Cys Thr His Gly Ile Lys Pro Val Val
210                 215                 220

Ser Thr Gln Leu Leu Leu Asn Gly Ser Leu Ala Glu Glu Ile Ile
225                 230                 235                 240

Ile Arg Ser Glu Asn Leu Thr Asn Asn Ala Lys Thr Ile Ile Val His
                245                 250                 255

Leu Asn Lys Ser Val Glu Ile Asn Cys Thr Arg Pro Ser Asn Asn Thr
            260                 265                 270

Arg Thr Ser Ile Thr Ile Gly Pro Gly Gln Val Phe Tyr Arg Thr Gly
        275                 280                 285

Asp Ile Ile Gly Asp Ile Arg Lys Ala Tyr Cys Glu Ile Asn Gly Thr
290                 295                 300

Lys Trp Asn Glu Val Leu Lys Gln Val Thr Gly Lys Leu Lys Glu His
305                 310                 315                 320

Phe Asn Asn Lys Thr Ile Ile Phe Gln Pro Pro Ser Gly Gly Asp Leu
                325                 330                 335

Glu Ile Thr Met His His Phe Asn Cys Arg Gly Glu Phe Phe Tyr Cys
            340                 345                 350

Asn Thr Thr Lys Leu Phe Asn Asn Thr Cys Ile Gly Asn Glu Thr Met
        355                 360                 365

Glu Gly Cys Asn Gly Thr Ile Ile Leu Pro Cys Lys Ile Lys Gln Ile
    370                 375                 380

Ile Asn Met Trp Gln Gly Val Gly Gln Ala Met Tyr Ala Pro Pro Ile
385                 390                 395                 400

Ser Gly Arg Ile Asn Cys Val Ser Asn Ile Thr Gly Ile Leu Leu Thr
                405                 410                 415

Arg Asp Gly Gly Ala Asn Asn Thr Ala Asn Glu Thr Phe Arg Pro Gly
            420                 425                 430

Gly Gly Asn Ile Lys Asp Asn Trp Arg Ser Glu Leu Tyr Lys Tyr Lys
        435                 440                 445

Val Val Gln Ile Glu Pro Leu Gly Ile Ala Pro Thr Arg Ala Lys Arg
    450                 455                 460

Arg Val Val Glu
465
```

```
<210> SEQ ID NO 11
<211> LENGTH: 460
<212> TYPE: PRT
<213> ORGANISM: Artificial Sequence
<220> FEATURE:
<223> OTHER INFORMATION: laboratory-synthesized sequences

<400> SEQUENCE: 11
```

| | | | | | | | | | | | | | | | |
|---|---|---|---|---|---|---|---|---|---|---|---|---|---|---|---|
| Leu | Trp | Val | Thr | Val | Tyr | Tyr | Gly | Val | Pro | Val | Trp | Lys | Glu | Ala | Thr |
| 1 | | | | 5 | | | | | 10 | | | | | 15 | |
| Thr | Thr | Leu | Phe | Cys | Ala | Ser | Asp | Ala | Lys | Ser | Tyr | Glu | Ala | Glu | Ala |
| | | | 20 | | | | | 25 | | | | | 30 | | |
| His | Asn | Ile | Trp | Ala | Thr | His | Ala | Cys | Val | Pro | Thr | Asp | Pro | Asn | Pro |
| | | | 35 | | | | 40 | | | | | 45 | | | |
| Gln | Glu | Ile | Val | Leu | Glu | Asn | Val | Thr | Glu | Asn | Phe | Asn | Ile | Trp | Lys |
| | 50 | | | | | 55 | | | | | 60 | | | | |
| Asn | Asn | Met | Val | Glu | Gln | Met | His | Asp | Asp | Ile | Ile | Ser | Leu | Trp | Asp |
| 65 | | | | | 70 | | | | | 75 | | | | | 80 |
| Gln | Ser | Leu | Lys | Pro | Cys | Val | Lys | Leu | Pro | Leu | Cys | Val | Thr | Leu |
| | | | | 85 | | | | | 90 | | | | | 95 |
| Asn | Cys | Thr | Glu | Trp | Lys | Asn | Ala | Thr | Thr | Asn | Ala | Thr | Asn | Glu | Gly |
| | | | 100 | | | | | 105 | | | | | 110 | | |
| Ile | Gly | Met | Lys | Asn | Cys | Ser | Phe | Thr | Glu | Val | Arg | Asp | Lys | Lys | Lys |
| | | | 115 | | | | | 120 | | | | | 125 | | |
| Gln | Ala | Tyr | Ala | Leu | Phe | Tyr | Lys | Leu | Asp | Val | Val | Gln | Met | Asn | Asp |
| | 130 | | | | | 135 | | | | | 140 | | | | |
| Asp | Asn | Ser | Thr | Asn | Thr | Ser | Tyr | Arg | Leu | Ile | Asn | Cys | Asn | Ala | Ser |
| 145 | | | | | 150 | | | | | 155 | | | | | 160 |
| Thr | Ile | Thr | Gln | Ala | Cys | Pro | Lys | Ile | Ser | Phe | Glu | Pro | Ile | Pro | Ile |
| | | | | 165 | | | | | 170 | | | | | 175 | |
| His | Tyr | Cys | Ala | Pro | Ala | Gly | Phe | Ala | Ile | Leu | Lys | Cys | Asn | Asp | Lys |
| | | | 180 | | | | | 185 | | | | | 190 | | |
| Lys | Phe | Asn | Gly | Thr | Gly | Pro | Cys | Lys | Asn | Val | Ser | Thr | Val | Gln | Cys |
| | | | 195 | | | | | 200 | | | | | 205 | | |
| Thr | His | Gly | Ile | Lys | Pro | Val | Val | Ser | Thr | Gln | Leu | Leu | Asn | Gly |
| | 210 | | | | | 215 | | | | | 220 | | | | |
| Ser | Leu | Ala | Glu | Glu | Glu | Ile | Ile | Ile | Arg | Ser | Glu | Asn | Leu | Thr | Asn |
| 225 | | | | | 230 | | | | | 235 | | | | | 240 |
| Asn | Ala | Lys | Ile | Ile | Ile | Val | His | Leu | Asn | Glu | Ser | Val | Pro | Ile | Asn |
| | | | | 245 | | | | | 250 | | | | | 255 | |
| Cys | Thr | Arg | Pro | Tyr | Asp | Lys | Val | Ser | Tyr | Arg | Thr | Pro | Ile | Gly | Val |
| | | | 260 | | | | | 265 | | | | | 270 | | |
| Gly | Arg | Ala | Ser | Tyr | Thr | Thr | Arg | Ile | Lys | Gly | Asp | Ile | Arg | Gln | Ala |
| | | | 275 | | | | | 280 | | | | | 285 | | |
| His | Cys | Asn | Ile | Ser | Gly | Glu | Lys | Trp | Asn | Lys | Thr | Leu | Gln | Gln | Val |
| | 290 | | | | | 295 | | | | | 300 | | | | |
| Ala | Ala | Lys | Leu | Arg | Asp | Leu | Leu | Asn | Gln | Thr | Ala | Ile | Ile | Phe | Lys |
| 305 | | | | | 310 | | | | | 315 | | | | | 320 |
| Pro | Ser | Ser | Gly | Gly | Asp | Pro | Glu | Ile | Thr | Thr | His | Ser | Phe | Asn | Cys |
| | | | | 325 | | | | | 330 | | | | | 335 | |
| Gly | Gly | Glu | Phe | Phe | Tyr | Cys | Asn | Thr | Ser | Gly | Leu | Phe | Asn | Asn | Ser |
| | | | 340 | | | | | 345 | | | | | 350 | | |
| Val | Trp | Thr | Ser | Asn | Ser | Thr | Ile | Gly | Ala | Asn | Gly | Thr | Ile | Thr | Leu |
| | | | 355 | | | | | 360 | | | | | 365 | | |
| Pro | Cys | Arg | Ile | Lys | Gln | Ile | Ile | Asn | Met | Trp | Gln | Gly | Val | Gly | Lys |

```
                370             375             380
Ala Met Tyr Thr Pro Pro Ile Glu Gly Gln Ile Asn Cys Ser Ser Thr
385                 390             395                 400

Ile Thr Gly Leu Leu Leu Thr Arg Asp Gly Val Lys Asn Asn Ser
                405             410             415

Gln Asn Glu Thr Phe Arg Pro Gly Gly Asp Met Arg Asp Asn Trp
            420             425             430

Arg Asn Glu Leu Tyr Lys Tyr Lys Val Val Arg Ile Glu Pro Leu Gly
        435             440             445

Leu Ala Pro Thr Lys Ala Arg Arg Val Val Glu
    450             455             460
```

<210> SEQ ID NO 12
<211> LENGTH: 473
<212> TYPE: PRT
<213> ORGANISM: Artificial Sequence
<220> FEATURE:
<223> OTHER INFORMATION: laboratory-synthesized sequences

<400> SEQUENCE: 12

```
Leu Trp Val Thr Val Tyr Tyr Gly Val Pro Val Trp Lys Glu Ala Asn
1               5                   10                  15

Thr Thr Leu Phe Cys Ala Ser Asp Ala Lys Ala Tyr Asp Thr Glu Val
                20                  25                  30

His Asn Val Trp Ala Thr His Ala Cys Val Pro Thr Asp Pro Asp Pro
            35                  40                  45

Gln Glu Val Glu Leu Glu Asn Val Thr Glu Asn Phe Asn Met Trp Lys
    50                  55                  60

Asn Asn Met Val Glu Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Thr Asn Leu Arg Asn Asp Thr Asn Thr Thr Arg Asn Ala Thr
            100                 105                 110

Asn Thr Thr Ser Ser Glu Thr Met Met Glu Glu Gly Glu Ile Lys Asn
        115                 120                 125

Cys Ser Phe Asn Ile Thr Thr Ser Ile Arg Asp Lys Val Gln Lys Glu
    130                 135                 140

Phe Ala Leu Phe Tyr Lys Leu Asp Val Val Pro Ile Glu Asn Asp Thr
145                 150                 155                 160

Thr Ser Tyr Arg Leu Ile Ser Cys Asn Thr Ser Val Leu Thr Gln Ala
                165                 170                 175

Cys Pro Lys Val Ser Phe Glu Pro Ile Pro Ile His Phe Cys Ala Pro
            180                 185                 190

Ala Gly Phe Ala Ile Leu Lys Cys Lys Asp Lys Lys Phe Asn Gly Thr
        195                 200                 205

Gly Pro Cys Thr Asn Val Ser Thr Val Gln Cys Thr His Gly Ile Lys
    210                 215                 220

Pro Val Val Ser Thr Gln Leu Leu Leu Asn Gly Ser Leu Ala Glu Glu
225                 230                 235                 240

Glu Val Val Ile Arg Ser Ala Asn Leu Ser Asp Asn Ala Lys Thr Ile
                245                 250                 255

Ile Val Gln Leu Asn Glu Ser Val Gln Met Asn Cys Thr Arg Pro Asn
            260                 265                 270

Asn Asn Thr Arg Lys Ser Ile His Ile Gly Pro Gly Arg Ala Phe Tyr
```

```
                    275                 280                 285
Thr Thr Gly Glu Ile Ile Gly Asp Ile Arg Gln Ala His Cys Asn Leu
290                 295                 300

Ser Arg Thr Lys Trp Asn Glu Thr Leu Lys Arg Ile Val Ile Lys Leu
305                 310                 315                 320

Arg Glu Gln Tyr Glu Asn Lys Thr Ile Val Phe Asn Gln Ser Ser Gly
                325                 330                 335

Gly Asp Pro Glu Ile Val Met Leu Ser Phe Asn Cys Gly Gly Glu Phe
            340                 345                 350

Phe Tyr Cys Asn Ser Thr Lys Leu Phe Asn Ser Thr Trp Asn Gly Thr
        355                 360                 365

Glu Ser Asn Asn Thr Gly Asp Asp Pro Ile Val Leu Pro Cys Arg Ile
370                 375                 380

Lys Gln Val Ile Asn Met Trp Gln Glu Val Gly Lys Ala Met Tyr Ala
385                 390                 395                 400

Pro Pro Ile Arg Gly Gln Ile Arg Cys Ser Ser Asn Ile Thr Gly Leu
                405                 410                 415

Leu Leu Thr Arg Asp Gly Gly Asn Ser Asn Glu Thr Asn Thr Thr Glu
            420                 425                 430

Ile Phe Arg Pro Gly Gly Gly Asn Met Lys Asp Asn Trp Arg Ser Glu
        435                 440                 445

Leu Tyr Lys Tyr Lys Val Val Arg Ile Glu Pro Leu Gly Ile Ala Pro
    450                 455                 460

Thr Arg Ala Lys Arg Arg Val Val Gln
465                 470

<210> SEQ ID NO 13
<211> LENGTH: 463
<212> TYPE: PRT
<213> ORGANISM: Artificial Sequence
<220> FEATURE:
<223> OTHER INFORMATION: laboratory-synthesized sequences

<400> SEQUENCE: 13

Leu Trp Val Thr Val Tyr Tyr Gly Val Pro Val Trp Lys Glu Ala Thr
1               5                   10                  15

Thr Thr Leu Phe Cys Ala Ser Asp Ala Lys Ala Tyr Asp Thr Glu Val
            20                  25                  30

His Asn Val Trp Ala Thr His Ala Cys Val Pro Thr Asp Pro Asn Pro
        35                  40                  45

Gln Glu Val Val Leu Gly Asn Val Thr Glu Asn Phe Asn Met Trp Lys
    50                  55                  60

Asn Asn Met Val Glu Gln Met His Glu Asp Ile Ile Ser Leu Trp Asp
65                  70                  75                  80

Gln Ser Leu Lys Pro Cys Val Lys Leu Thr Pro Leu Cys Val Thr Leu
                85                  90                  95

Asn Cys Thr Asp Leu Arg Asn Ala Thr Asn Thr Ser Ser Thr Met Glu
            100                 105                 110

Gly Gly Glu Ile Lys Asn Cys Ser Phe Asn Ile Thr Thr Ser Ile Lys
        115                 120                 125

Thr Lys Val Lys Asp Tyr Ala Leu Phe Tyr Lys Leu Asp Val Val Pro
    130                 135                 140

Ile Asp Asn Asp Asn Thr Ser Tyr Arg Leu Ile Asn Cys Asn Thr Ser
145                 150                 155                 160

Val Ile Thr Gln Ala Cys Pro Lys Val Ser Phe Glu Pro Ile Pro Ile
```

```
                 165                 170                 175

His Tyr Cys Thr Pro Ala Gly Phe Ala Ile Leu Gln Cys Asn Asn Lys
            180                 185                 190

Lys Phe Asn Gly Thr Gly Pro Cys Thr Asn Val Ser Thr Val Gln Cys
        195                 200                 205

Thr His Gly Ile Arg Pro Val Val Ser Thr Gln Leu Leu Leu Asn Gly
    210                 215                 220

Ser Leu Ala Glu Glu Val Val Ile Arg Ser Ser Asn Phe Thr Asp
225                 230                 235                 240

Asn Ala Arg Val Ile Ile Val Gln Leu Asn Glu Ser Val Glu Ile Asn
                245                 250                 255

Cys Thr Arg Pro Asn Asn Asn Thr Arg Lys Ser Ile His Leu Gly Pro
            260                 265                 270

Gly Arg Ala Trp Tyr Thr Thr Gly Gln Ile Ile Gly Asp Ile Arg Gln
        275                 280                 285

Ala His Cys Asn Leu Ser Ser Thr Lys Trp Asn Asn Thr Leu Arg Gln
    290                 295                 300

Ile Thr Glu Lys Leu Arg Glu Gln Phe Gly Asn Lys Thr Ile Val Phe
305                 310                 315                 320

Asn Gln Ser Ser Gly Gly Asp Pro Glu Ile Val Met His Ser Phe Asn
                325                 330                 335

Cys Gly Gly Glu Phe Phe Tyr Cys Asn Thr Thr Gln Leu Phe Asn Ser
            340                 345                 350

Thr Trp Asn Asp Thr Ser Thr Trp Asn Asn Thr Gly Asn Gly Thr
        355                 360                 365

Ile Thr Leu Pro Cys Arg Ile Lys Gln Ile Val Asn Met Trp Gln Glu
    370                 375                 380

Val Gly Lys Ala Met Tyr Ala Pro Pro Ile Arg Gly Gln Ile Arg Cys
385                 390                 395                 400

Ser Ser Asn Ile Thr Gly Leu Leu Leu Thr Arg Asp Gly Gly Asn Ser
                405                 410                 415

Glu Asn Lys Thr Thr Glu Thr Phe Arg Pro Gly Gly Gly Asp Met Arg
            420                 425                 430

Asp Asn Trp Arg Ser Glu Leu Tyr Lys Tyr Lys Val Val Lys Ile Glu
        435                 440                 445

Pro Leu Gly Val Ala Pro Thr Lys Pro Lys Arg Arg Val Val Gln
    450                 455                 460

<210> SEQ ID NO 14
<211> LENGTH: 466
<212> TYPE: PRT
<213> ORGANISM: Artificial Sequence
<220> FEATURE:
<223> OTHER INFORMATION: laboratory-synthesized sequences

<400> SEQUENCE: 14

Leu Trp Val Thr Val Tyr Tyr Gly Val Pro Val Trp Lys Asp Ala Lys
1               5                   10                  15

Thr Thr Leu Phe Cys Ala Ser Asp Ala Lys Ala Tyr Glu Arg Glu Val
            20                  25                  30

His Asn Val Trp Ala Thr His Ala Cys Val Pro Thr Asp Pro Asn Pro
        35                  40                  45

Gln Glu Ile Val Trp Glu Asn Val Thr Glu Asn Phe Asn Met Trp Lys
    50                  55                  60

Asn Asp Ile Val Asp Gln Met His Glu Asp Ile Ile Ser Leu Trp Asp
```

```
                65                  70                  75                  80
        Gln Ser Leu Lys Pro Cys Val Lys Leu Thr Pro Leu Cys Val Thr Leu
                            85                  90                  95

Asn Cys Ser Asn Ala Asn Asn Thr Ala Thr Asn Asn Val Thr Ala Thr
                        100                 105                 110

Asn Asn Val Thr Ser Asp Met Lys Asn Cys Ser Phe Asn Ala Thr Thr
                    115                 120                 125

Glu Leu Arg Asp Lys Arg Gln Lys Val Tyr Ala Leu Phe Tyr Lys Leu
                130                 135                 140

Asp Ile Val Pro Leu Asn Glu Lys Asp Asn Ser Ser Ser Gly Glu Tyr
        145                 150                 155                 160

Arg Leu Ile Asn Cys Ser Thr Ser Thr Val Thr Gln Ala Cys Pro Lys
                        165                 170                 175

Val Ser Phe Asp Pro Ile Pro Ile His Tyr Cys Thr Pro Ala Gly Tyr
                    180                 185                 190

Ala Ile Leu Lys Cys Asn Asn Lys Thr Phe Asn Gly Thr Gly Pro Cys
                195                 200                 205

His Asn Val Ser Thr Val Gln Cys Thr His Gly Ile Lys Pro Val Val
            210                 215                 220

Ser Thr Gln Leu Leu Leu Asn Gly Ser Leu Ala Glu Gly Glu Ile Ile
        225                 230                 235                 240

Ile Arg Ser Glu Asn Leu Thr Asn Asn Val Lys Thr Ile Ile Val His
                        245                 250                 255

Leu Asn Glu Ser Val Glu Ile Val Cys Thr Arg Pro Asn Asn Asn Thr
                    260                 265                 270

Arg Arg Ser Ile Arg Ile Gly Pro Gly Gln Val Phe Tyr Ala Asn Asn
                275                 280                 285

Asp Ile Ile Gly Asp Ile Arg Gln Ala His Cys Asn Ile Ser Lys Asp
        290                 295                 300

Val Trp Asn Ser Thr Leu Gln Lys Val Gly Lys Lys Leu Lys Glu His
        305                 310                 315                 320

Phe Pro Asn Lys Thr Ile Thr Phe Glu Pro His Ser Gly Gly Asp Leu
                        325                 330                 335

Glu Ile Thr Thr His Ser Phe Asn Cys Arg Gly Glu Phe Phe Tyr Cys
                    340                 345                 350

Asn Thr Ser Gly Leu Phe Asn Ser Asn Phe Asn Asp Thr Glu Gly Asn
                355                 360                 365

Ser Thr Leu Ser Ile Thr Leu Pro Cys Arg Ile Lys Gln Ile Ile Asn
        370                 375                 380

Met Trp Gln Glu Val Gly Arg Ala Met Tyr Ala Pro Pro Ile Glu Gly
        385                 390                 395                 400

Asn Ile Thr Cys Lys Ser Asn Ile Thr Gly Leu Leu Leu Thr Arg Gly
                        405                 410                 415

Gly Gly Pro Thr Asn Thr Lys Thr Glu Thr Phe Arg Pro Gly Gly Gly
                    420                 425                 430

Asp Met Arg Asp Asn Trp Arg Ser Glu Leu Tyr Lys Tyr Lys Val Val
                435                 440                 445

Glu Ile Lys Pro Leu Gly Val Ala Pro Thr Lys Ala Lys Arg Arg Val
            450                 455                 460

Val Glu
        465

<210> SEQ ID NO 15
```

<211> LENGTH: 1626
<212> TYPE: DNA
<213> ORGANISM: Artificial Sequence
<220> FEATURE:
<223> OTHER INFORMATION: laboratory-synthesized sequences

<400> SEQUENCE: 15

| | | | | | | |
|---|---|---|---|---|---|---|
| aatattggct | attggccatt | gcatacgttg | tatctatatc | ataatatgta | catttatatt | 60 |
| ggctcatgtc | caatatgacc | gccatgttga | cattagttat | tgactagtta | ttaatagtaa | 120 |
| tcaattacgg | ggtcattagt | tcatagccca | tatatggagt | tccgcgttac | ataacttacg | 180 |
| gtaaatggcc | cgcctggctg | accgcccaac | gacccccgcc | cattgacgtc | aataatgacg | 240 |
| tatgttccca | tagtaacgcc | aatagggact | ttccattgac | gtcaatgggt | ggagtattta | 300 |
| cggtaaactg | cccacttggc | agtacatcaa | gtgtatcata | tgccaagtcc | gccccctatt | 360 |
| gacgtcaatg | acggtaaatg | gcccgcctgg | cattatgccc | agtacatgac | cttacgggac | 420 |
| tttcctactt | ggcagtacat | ctacgtatta | gtcatcgcta | ttaccatggt | gatgcggttt | 480 |
| tggcagtaca | ccaatgggcg | tggatagcgg | tttgactcac | ggggatttcc | aagtctccac | 540 |
| cccattgacg | tcaatgggag | tttgttttgg | caccaaaatc | aacgggactt | tccaaaatgt | 600 |
| cgtaataacc | ccgccccgtt | gacgcaaatg | ggcggtaggc | gtgtacggtg | ggaggtctat | 660 |
| ataagcagag | ctcgtttagt | gaaccgtcag | atcgcctgga | gacgccatcc | acgctgtttt | 720 |
| gacctccata | gaagacaccg | ggaccgatcc | agcctccgcg | gccgggaacg | gtgcattgga | 780 |
| acgcggattc | cccgtgccaa | gagtgacgta | agtaccgcct | atagactcta | taggcacacc | 840 |
| cctttggctc | ttatgcatgc | tatactgttt | ttggcttggg | gcctatacac | ccccgctcct | 900 |
| tatgctatag | gtgatggtat | agcttagcct | ataggtgtgg | gttattgacc | attattgacc | 960 |
| actcccctat | tggtgacgat | actttccatt | actaatccat | aacatggctc | tttgccacaa | 1020 |
| ctatctctat | tggctatatg | ccaatactct | gtccttcaga | gactgacacg | gactctgtat | 1080 |
| ttttacagga | tggggtccca | tttattattt | acaaattcac | atatacaaca | acgccgtccc | 1140 |
| ccgtgcccgc | agtttttatt | aaacatagcg | tgggatctcc | acgcgaatct | cgggtacgtg | 1200 |
| ttccggacat | gggctcttct | ccggtagcgg | cggagcttcc | acatccgagc | ctggtccca | 1260 |
| tgcctccagc | ggctcatggt | cgctcggcag | ctccttgctc | ctaacagtgg | aggccagact | 1320 |
| taggcacagc | acaatgccca | ccaccaccag | tgtgccgcac | aaggccgtgg | cggtagggta | 1380 |
| tgtgtctgaa | aatgagctcg | gagattgggc | tcgcaccgct | gacgcagatg | gaagacttaa | 1440 |
| ggcagcggca | gaagaagatg | caggcagctg | agttgttgta | ttctgataag | agtcagaggt | 1500 |
| aactcccgtt | gcggtgctgt | taacggtgga | gggcagtgta | gtctgagcag | tactcgttgc | 1560 |
| tgccgcgcgc | gccaccagac | ataatagctg | acagactaac | agactgttcc | tttccatggg | 1620 |
| tctttt | | | | | | 1626 |

<210> SEQ ID NO 16
<211> LENGTH: 63
<212> TYPE: DNA
<213> ORGANISM: Artificial Sequence
<220> FEATURE:
<223> OTHER INFORMATION: laboratory-synthesized sequences

<400> SEQUENCE: 16

| | | | | | | |
|---|---|---|---|---|---|---|
| atggatgcaa | tgaagagagg | gctctgctgt | gtgctgctgc | tgtgtggagc | agtcttcgtt | 60 |
| tcg | | | | | | 63 |

COMPOSITIONS AND METHODS TO TREAT AIDS

CROSS REFERENCE TO RELATED APPLICATIONS

This application is a national stage application under 35 U.S.C. 371 of International Patent Application No. PCT/US2014/026247, filed on Mar. 13, 2014, which claims priority to U.S. Provisional Patent Application Ser. No. 61/788,837, filed on Mar. 15, 2013, the disclosure of each of these applications which is incorporated herein by reference in its entirety.

STATEMENT OF FEDERALLY SPONSORED RESEARCH

This invention was made with government support under Grant No. AI082676 awarded by the National Institutes of Health. The Government has certain rights in the invention.

TECHNICAL FIELD

The invention relates to compositions and methods for the treatment of acquired immunodeficiency syndrome (AIDS).

BACKGROUND

Human immunodeficiency virus (HIV) is the etiological agent of Acquired Immune Deficiency Syndrome (AIDS). There are two types of HIV currently recognized, HIV-1 and HIV-2. HIV-1 is the predominant form worldwide. There are three HIV-1 groups, the major group (M group), the outlier group (O group), and the non-M/non-O group (N group). The M group is further divided into at least eleven distinct genetic subtypes that are commonly referred to as subtypes or clades: A, B, C, D, E, F, G, H, I, J, and K. Subtype B is the most prevalent in the United States, while subtype C is the most prevalent worldwide. Geographic distribution of genetic subtypes is continually changing, and current data offers incomplete estimates.

Approximately 95% of new HIV infections occur in developing countries, thus a vaccine may be the most effective way to control the epidemic. However, developing effective vaccines to inhibit, reduce, or neutralize HIV infection has been a difficult challenge to the scientific community. It is a primary goal to develop an HIV vaccine that can effectively elicit broad and balanced anti-viral immunity, including protective antibody responses, and in particular, neutralizing antibody (NAb) and cell-mediated immune responses to control the spread of HIV. The extraordinary degree of genetic diversity of HIV has been problematic for vaccine development.

SUMMARY

The compositions and methods provided herein are based, at least in part, on the discovery that specific polyvalent, primary isolate DNA vaccines can effectively induce an immune response against HIV (e.g., HIV-1), e.g., alone or in combination with boosts of recombinant HIV polypeptide compositions. In general, the disclosure features nucleic acid compositions including or consisting of a single set or a plurality of sets of synthetic, codon-optimized nucleic acid molecules, e.g., DNA plasmids, each nucleic acid molecule encoding an HIV, e.g., HIV-1, envelope glycoprotein, wherein each set of nucleic acid molecules encodes a different type of HIV envelope glycoprotein, or comprises or consists of a primary isolate sequence from a distinct genetic clade. The nucleic acid molecules can be codon-optimized nucleotide sequences that have at least or about 90%, e.g., at least or about 92%, 95%, 96%, 97%, 98%, 99%, or 100%, identity to the nucleotide sequence of SEQ ID NO:1, 3, 5, 7, or 9. The encoded proteins can be wild-type sequences, or can include conservation amino acid substitutions, e.g., at 1 in 10, 1 in 20, 1 in 30, or fewer, e.g., at 1, 2, 5, or 10 total amino acid locations per protein. In certain embodiments, consensus sequences (based on a collection of different wild-type sequences) can be used.

In various embodiments, the HIV envelope glycoprotein can be gp120. The envelope glycoproteins can be from a clade of a major (M) group of clades, e.g., the clade can be clade A, B, C, D, or A/E. For example, the envelope glycoprotein can be an envelope glycoprotein of a 92UG037.1 (clade A), JR-FL (clade B), 93MW965.26 (clade C), 92UG021.16 (clade D), gp120-A/E-cons (clade A/E), UG21-9 (clade A), 92US715.6 (clade B), JR-FL (clade B), TH14.12 (clade B), 93MW959 (clade C) isolate, or any combination thereof.

In another aspect, the disclosure includes nucleic acid compositions that include or consist of a plurality of sets of nucleic acid molecules, wherein the plurality includes or consists of two or more of the following sets: a set of nucleic acid molecules, each encoding a HIV envelope glycoprotein of clade A; a set of nucleic acid molecules, each encoding a HIV envelope glycoprotein of clade B; a set of nucleic acid molecules, each encoding a HIV envelope glycoprotein of clade C; each encoding a HIV envelope glycoprotein of clade D; and a set of nucleic acid molecules, each encoding a HIV envelope glycoprotein of clade A/E; wherein each set of nucleic acid molecules encodes a primary isolate sequence of the envelope glycoprotein. For example, the nucleic acid molecules can be codon-optimized nucleotide sequences that have at least or about 90%, e.g., at least or about 92%, 95%, 96%, 97%, 98%, 99%, or 100%, identity to the nucleotide sequence of SEQ ID NO:1, 3, 5, 7, or 9. Also provided herein are polypeptides that have an amino acid sequence that has at least or about 90%, e.g., at least or about 92%, 95%, 96%, 97%, 98%, 99%, or 100%, identity to all or portions of the amino acid sequences of the polypeptides represented by SEQ ID NO:2, 4, 6, 8, 10, 11, 12, 13, or 14.

In various embodiments, the compositions can contain between 50 µg and 2,500 µg of nucleic acid of each set.

In another aspect, the disclosure includes pharmaceutical compositions containing one or more of the new compositions described herein and a pharmaceutically acceptable excipient. In various embodiments, the HIV envelope glycoproteins described herein are expressed in cells, e.g., bacterial or mammalian cells, e.g., CHO cells, and harvested and/or purified from the culture medium in the presence of a divalent metal ion, e.g., a divalent metal ion salt such as $ZnCl_2$, $CuSO_4$, $CoSO_4$, $NiSO_4$, and $CaCl_2$, in an amount sufficient to reduce or inhibit degradation of the envelope glycoproteins in the culture medium.

The disclosure also features methods of treating an individual with AIDS, by administering to the individual an amount of the new pharmaceutical compositions sufficient to inhibit disease progression due to HIV. In these methods, the mode of administration can be topical administration, oral administration, injection by needle, needle-less jet injection, intradermal administration, intramuscular administration, and gene gun administration. The immune response can be a protective immune response, e.g., a cell-mediated immune response, a humoral immune response, or both.

In certain methods, the new compositions can be administered in combination with a second therapy for HIV infection, e.g., therapy with a nucleoside reverse transcriptase inhibitor, therapy with a non-nucleoside reverse transcriptase inhibitor, and/or therapy with a HIV protease inhibitor.

The disclosure also includes methods of inducing an immune response against HIV or an HIV epitope in a vertebrate mammal by administering to the mammal an amount of the new compositions sufficient to elicit an immune response against HIV or an HIV epitope in the vertebrate mammal. These methods can further include isolating immune cells from the vertebrate mammal; and testing an immune response of the isolated immune cells in vitro. In these methods, the composition can be administered in multiple doses over an extended period of time, (e.g., over a period of 2, 3, 4 weeks or more, e.g., several months).

The methods can also include administering an adjuvant, boost, or facilitating agent before, at the same time as, or after administration of the composition. The vertebrate mammals can be a mouse, a rat, a rabbit, a non-human primate, or a human, e.g., a human infected with, or at risk for infection by, HIV. The mode of administration can be topical administration, oral administration, injection by needle, needle-less jet injection, intramuscular administration, intradermal administration, and gene gun administration.

In another aspect, the disclosure features isolated polypeptide compositions including or consisting of a set of isolated HIV envelope glycoprotein molecules, wherein each molecule in the set includes a primary isolate sequence.

The disclosure also includes polypeptide compositions that include or consist of a plurality of sets of isolated HIV, e.g., HIV-1, envelope glycoprotein molecules, wherein each molecule in the sets includes a different type of HIV envelope glycoprotein, or a primary isolate sequence from a distinct genetic clade. For example, the envelope glycoprotein of each set can be gp120. The clades and isolates can be the same as described herein for the nucleic acid compositions. The polypeptide compositions can be included in pharmaceutical compositions that include a pharmaceutically acceptable excipient.

In another aspect, the disclosure includes methods of inducing an immune response against HIV or a HIV epitope in a vertebrate mammal by administering to the mammal one or more of the nucleic acid compositions, and administering to the mammal one or more of the new polypeptide compositions; wherein the nucleic acid composition and/or the polypeptide composition are administered in amounts sufficient to elicit a detectable immune response against HIV or an HIV epitope in the vertebrate mammal. One can also isolate immune cells from the vertebrate mammal and test an immune response of the isolated immune cells in vitro.

In these methods, the new polypeptide compositions can be administered after the nucleic acid compositions, e.g., between 4 and 8 weeks after the nucleic acid compositions. In addition, a cell-mediated immune response can be tested, a humoral immune response can be tested, and/or a neutralizing humoral response can be tested.

A "vaccine" is a composition that induces an immune response in the recipient or host of the vaccine. Compositions and methods described herein cover a nucleic acid, e.g., DNA plasmid, vaccine that induces humoral (e.g., neutralizing antibody) responses and/or cell-mediated immune response (e.g., cytotoxic T lymphocyte (CTL)) responses in the recipient as protection against current or future HIV (e.g., HIV-1) infection. The vaccine can induce protection against infection upon subsequent challenge with HIV. Protection refers to resistance (e.g., partial resistance) to persistent infection of a host animal with HIV. Neutralizing antibodies generated in the vaccinated host can provide this protection. In other situations, CTL responses can provide this protection. In some situations, both neutralizing antibodies and cell-mediated immune (e.g., CTL) responses provide this protection.

Protective responses can be evaluated by a variety of methods. For example, the generation of neutralizing antibodies against HIV proteins (e.g., envelope glycoproteins, "Env gps"), and the generation of a cell-mediated immune response against HIV proteins can both indicate a protective response. Protective responses also include those responses that result in lower viral loads (e.g., in the blood or in lymphoid organs) in a vaccinated host animal exposed to a given inoculum of virus as compared to a host animal exposed to the inoculum of virus, and that has not been administered the vaccine.

"Polyvalency" and "multivalency" are used interchangeably herein and refer to a feature of a nucleic acid or polypeptide composition, e.g., DNA vaccine or protein/polypeptide composition, e.g., a protein boost composition. Each nucleic acid, e.g., plasmid, encodes either a different HIV envelope glycoprotein (Env gp) or Env gp in the form of defective HIV viral particles, or an HIV envelope glycoprotein from different clades, or a combination of these possibilities, allowing for flexibility of this polyvalent nucleic acid, e.g., DNA plasmid, vaccine. As used herein, "envelope glycoproteins" (Env gps) refer not only to isolated Env gps, but also to Env gps in the form of defective viral particles. "2-valent" refers to a composition of two distinct antigens (e.g., an Env antigen of a clade A isolate and an Env antigen of a clade B isolate). Likewise, "3-valent," "4-valent," and "5-valent" refer to compositions with three, four, and five unique antigens, respectively.

"Primary viral isolate" or "primary isolate" nucleic acid or amino acid sequences refer to nucleic acid or amino acid sequences from the cells or sera of individuals infected with HIV (e.g., HIV-1) rather than from a laboratory strain of HIV. A primary viral isolate is a viral isolate that has been expanded and maintained only in primary human T cells, monocytes, and/or macrophages, and has not been expanded and maintained in cell lines. Thus, a primary isolate differs from what is referred to as a "laboratory strain."

Laboratory strains of HIV have been passaged extensively in the laboratory, in some cases for many years. They may be referred to as TCLA strains, which stands for either tissue culture laboratory adapted strains or T cell line adapted strains. On the other hand, primary viral isolates are collected from the field (e.g., from infected human patients) and expanded or passaged in the laboratory, for example, only for the purpose of determining whether or not growth of the virus is possible, and then subsequently one can obtain the viral sequence. Expansion or passaging of the primary isolates occurs by co-culturing the virus with peripheral blood mononuclear cells, for example, to determine if viral growth can occur. The amount of expansion/passaging is dependent on the particular virus and can vary, but in any case, expansion/passaging is considered minimal or limited. This minimal or limited passaging is what differentiates a primary viral isolate from a laboratory strain.

The various aspects of the inventions described herein provide several advantages. Because of their polyvalency, the new vaccines are less likely to lose their efficacy due to the high mutation rate of HIV. The nucleic acid vaccines described herein provide many different antigens in the form of sequences from distinct genetic clades and thus single mutations of the infecting virus will not readily decrease the vaccines' effectiveness in recipients. Another advantage the invention provides is the induction of broader immune responses, because the different proteins are encoded by primary viral isolate sequences rather than laboratory strains.

Given the large number of mutated HIV-1 virus isolates, it is difficult to decide which Env antigens should be included in a vaccine. The present disclosure provides a small subset of gp120 immunogens that are better able to induce broad and potent neutralizing antibodies against a wide spectrum of HIV-1 viruses. This is significantly different from previous HIV vaccines that include randomly selected antigens. For example, the previously reported DP6-001 vaccine formulation (Wang et al., *Vaccine* 26:3947-3957, 2008) includes Env immunogens that elicit only narrow antibody responses.

The administration of both polyvalent DNA compositions and protein boosts (or protein-based vaccines and protein boosts) can elicit robust humoral and cell-mediated immune responses. The use of the combinations of compositions described herein provides neutralizing antibody responses. The presence of humoral and cell-mediated responses affords better protection from infection in naïve individuals. The presence of humoral and cell-mediated immune responses can delay disease progression in individuals that are infected with the virus prior to vaccination.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. Other features and advantages of the invention will be apparent from the following detailed description, the drawings, and from the claims.

DETAILED DESCRIPTION

Figure 1:
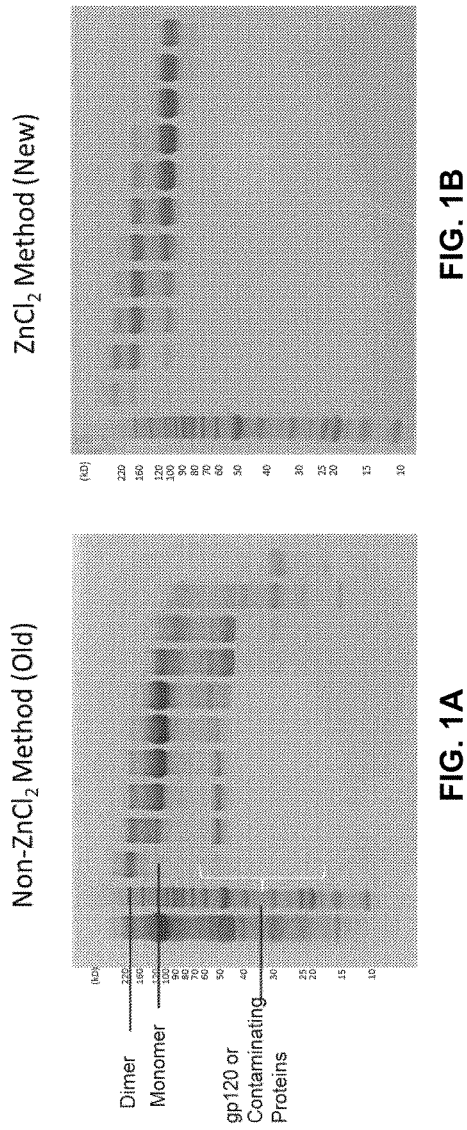
FIGS. 1A and 1B are two photomicrographs of a Western blot comparing purification of gp120 proteins from culture medium without $ZnCl_2$ (left panel) and with $ZnCl_2$ (right panel).
Figure 2:
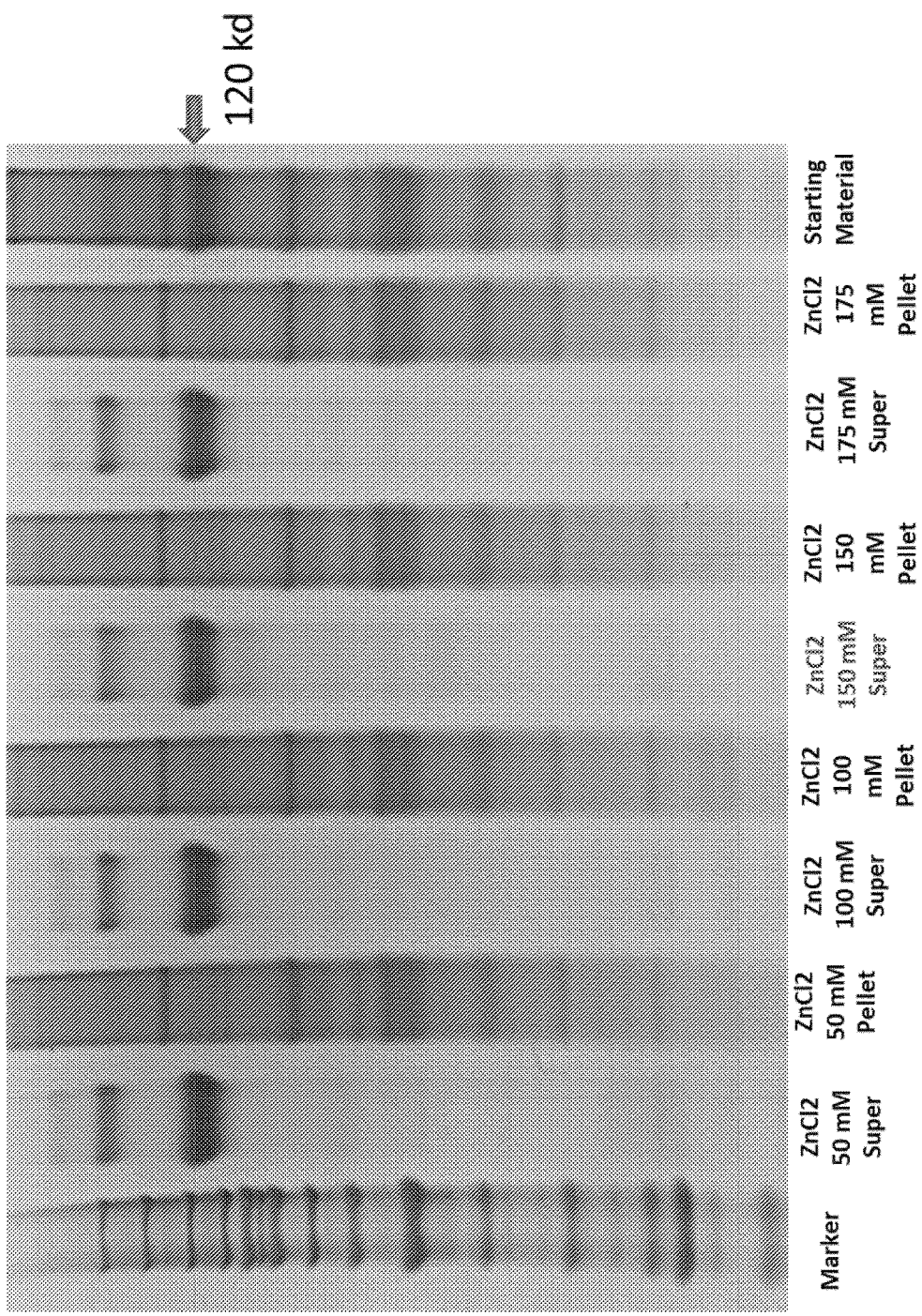
FIG. 2 is a photomicrograph of a Western blot showing that precipitation with zinc chloride removed most contaminating proteins.
Figure 3:
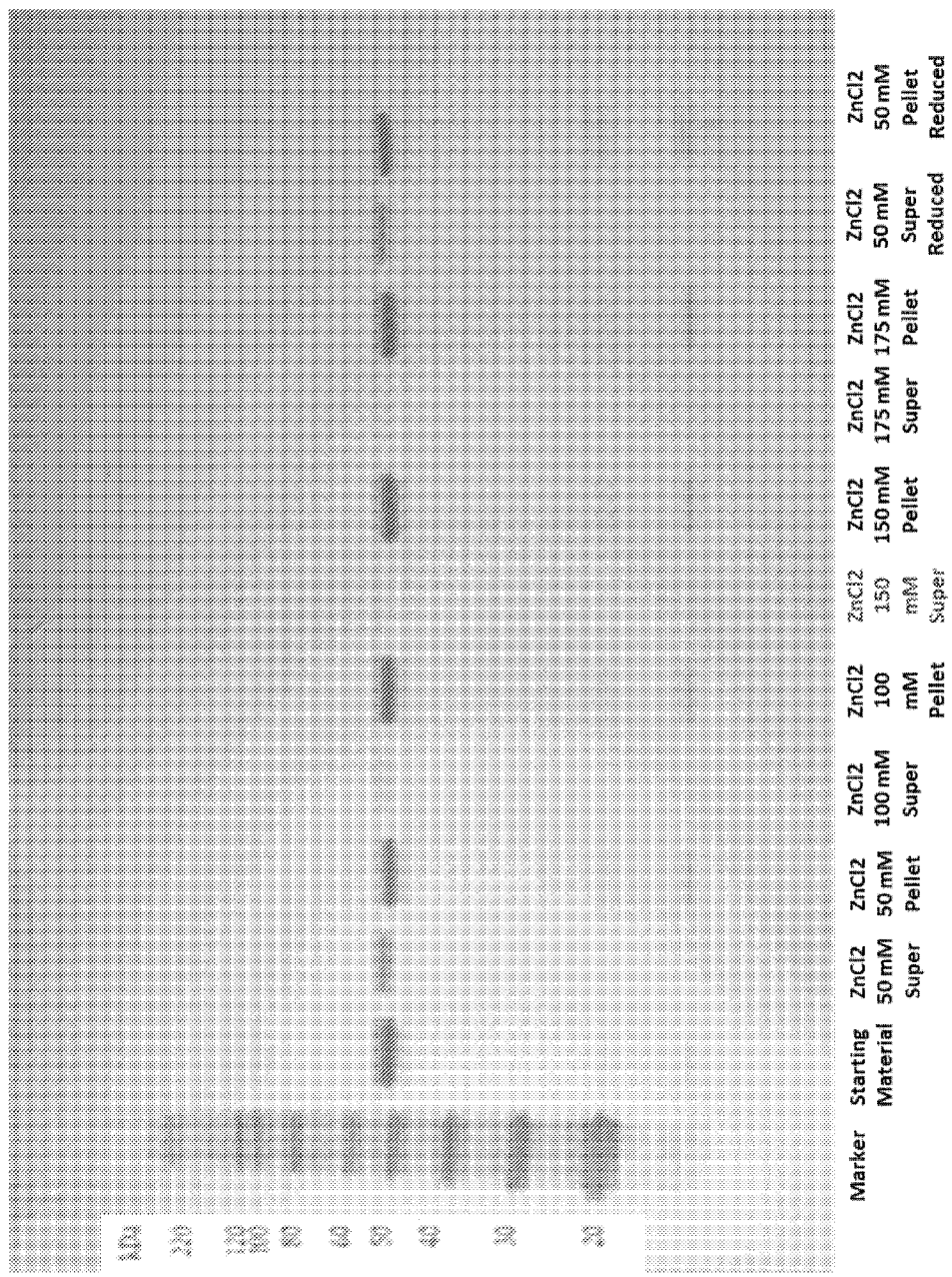
FIG. 3 is a photomicrograph of a Western blot with anti-fucosidase antibody demonstrating that precipitation with zinc chloride removed most contaminating proteins.

The compositions and methods described herein are based, at least in part, on the finding that specific codon-optimized primary HIV-1 isolates from multiple different genetic subtypes of HIV can be administered as a nucleic acid or polypeptide to induce broad antibody responses (e.g., neutralizing antibody responses) and cell-mediated immune responses (e.g., cytotoxic T lymphocyte (CTL)). These synthetic nucleic acid molecules and polypeptides can be combined or pooled together to create polyvalent DNA and polypeptide compositions, respectively. Recent strategies have suffered from only minimal immune protection due to escape from CTL recognition (Barouch et al., 2002, Nature, 415:335-339; Goulder et al., 2001, Nature, 412:334-338; Goulder et al., 1997, Nature Med., 3:212-217). To address this problem, nucleic acid sequences from primary HIV-1 isolates were used to generate polyvalent immune compositions, thus improving cell-mediated immune responses and decreasing the likelihood of CTL escape by the virus, as well as improving neutralizing antibody response. The new methods provide for flexibility in designing compositions based on combinations of vectors encoding different HIV-1 proteins and combinations of HIV-1 proteins.

Protein boosts can also be used in conjunction with the new DNA and protein-based vaccines. The protein boosts can include HIV proteins corresponding to all of the proteins encoded by DNA administered in prior DNA vaccination steps. Alternatively, a subset of proteins corresponding to the DNA vaccine is administered. In another embodiment, a group of unrelated envelope glycoproteins is administered. For example, if DNA encoding five different HIV proteins is administered (e.g., Env genes from five different HIV-1 isolates), the subsequent protein boost(s) can include all five of the Env proteins, four of the Env proteins, or fewer.

The DNA and polypeptide compositions can include different genes and proteins from different HIV isolates. In some embodiments, Env antigens are encoded by synthetic codon-optimized DNA compositions, and the Env antigens are included in the polypeptide compositions. Accordingly, provided herein are compositions comprising Env glycoproteins (gps), a combination of codon-optimized vectors encoding Env glycoproteins derived from the sequences of more than one HIV-1 primary isolate, e.g., clade A, B, C, D, and A/E, e.g., 92UG037.1 (clade A), JR-FL (clade B), 93MW965.26 (clade C), 92UG021.16 (clade D), gp120-A/E-cons (clade A/E), or any combination thereof. Since there are limited numbers of wild-type A/E gp120 antigens available, a subtype A/E consensus gp120 immunogen was designed (gp120-A/E-cons) based on available A/E Env sequences from Genbank.

Codon-optimized sequences for primary HIV-1 Env gps can be cloned into nucleic acid, e.g., DNA, vaccine vectors to produce a panel of DNA vaccine plasmids. The HIV envelope is the predominant target of neutralizing antibodies in HIV-infected individuals. Thus, a vaccine encoding Env gps can be used to induce neutralizing antibodies. The primary HIV-1 Env gps include gp120. To prepare the new vaccines, gp120 Env can be encoded by nucleic acids, e.g., DNA, from primary isolates covering five genetic clades, A, B, C, D, and A/E of the HIV-1 major group. These sequences were isolated from distinct geographic regions: North America, Africa, Asia, and South America.

Because of the genetic diversity of HIV, the vaccines based on antigens from laboratory strains of HIV-1, as opposed to primary isolates, have been limited in their ability to generate broad immune responses against the prevalent HIV primary strains (see, e.g., Barouch et al., 2002, Nature, 415:335-339; Johnston and Flores, 2001, Curr. Op. In. Pharmac., 1:504-510; and Mascola et al., 1996, J. Infect. Dis. 173:340-348). By combining multiple nucleic acid molecules (e.g., DNA plasmids) encoding primary isolate proteins (e.g., multiple Env gps) into one polyvalent vaccine, the new vaccines provide a considerable breadth of reactivity across genetic clades. Primary isolate DNA can be directly collected from HIV infected patients, passaged minimally if at all, sequenced, codon-optimized, and cloned into multiple DNA vaccine vectors to make a polyvalent vaccine. Minimal passaging may be required to expand the DNA if not enough DNA is available for sequencing. This polyvalent vaccine elicits a broad immune response and broad neutralization against Env gps from the different isolates. The polyvalency decreases the likelihood of low efficacy caused by the constantly changing genetic diversification and mutation of HIV.

Nucleic Acid Vaccines

Vaccines are useful in inhibiting, reducing, and/or neutralizing infection or disease by inducing immune responses to an antigen or antigens in an individual. For example, vaccines can be used prophylactically in naïve subjects identified as at risk for HIV, or therapeutically in subjects already infected or suspected to be infected with HIV. Skilled practitioners will appreciate that a subject can be identified as at risk for HIV or AIDS by any method known in the art, e.g., by a physician or other medical personnel. In some embodiments, the methods of diagnosis described herein are performed in conjunction with a standard HIV/AIDS workup, e.g., including laboratory tests (e.g., complete blood count (CBC); CD4 cell count; measurement of HIV RNA level; and cervical and anal Pap smears). Traditional vaccines, which include inactivated viruses or subunit protein antigen, have had poor immunogenicity, poor cell-mediated immunity induction, safety and stability concerns, and low efficacy. The development of nucleic acid vaccines has proved to be promising.

Codon-optimized forms of nucleic acids encoding gp120 Env gps such as 92UG037.1 (clade A), JR-FL (clade B), 93MW965.26 (clade C), 92UG021.16 (clade D), and gp120-A/E-cons (clade A/E), are useful for expressing such polypeptides in appropriate host cells. Codon-optimization permits more efficient expression than expression achieved using codons native to the virus. Enhanced expression is useful for producing large quantities of polypeptides for therapeutic and diagnostic applications. Nucleic acids encoding HIV antigens that are efficiently expressed in mammalian host cells are useful, e.g., for inducing immune responses to the antigens in the host, e.g., a human. The nucleic acid sequences described herein may induce higher levels of specific antibodies to HIV when administered to an animal (as compared to nucleic acid sequences which are not codon-optimized). In various embodiments, the nucleic acid sequences induce a neutralizing humoral immune response and/or a cell-mediated immune response when expressed in a mammalian subject. Codon-optimized nucleic acids can be constructed by synthetic means, obviating the need to obtain nucleic acids from live virus and/or increasing the ease of manipulation of sequences.

The new synthetic, codon-optimized DNA vaccines have the advantage of being more resilient to the rapid evolution and mutation of HIV due to their polyvalency. The new DNA vaccines have an added advantage of being derived from primary isolates, which in combination with their polyvalency can induce broader immune response, namely more effective neutralizing antibodies against HIV (e.g., HIV-1) and/or cell-mediated immune responses (e.g., cytotoxic T lymphocyte (CTL)), thus providing a more effective HIV vaccine. The combination of polyvalency and derivation from primary isolate DNA described herein confers its advantages as a novel vaccine for HIV (e.g., HIV-1).

In one aspect, the invention features synthetic, codon-optimized nucleic acid molecules encoding gp120 Env gps from 92UG037.1 (clade A), JR-FL (clade B), 93MW965.26 (clade C), 92UG021.16 (clade D), or gp120-A/E-cons (clade A/E), that do not occur naturally. A nucleotide sequence encoding an example of a codon-optimized gp120 Env gp from 92UG037.1 is provided as SEQ ID NO:1. The amino acid sequence encoded by SEQ ID NO:1 is provided as SEQ ID NO:2. A nucleotide sequence encoding an example of a codon-optimized gp120 Env gp from JR-FL is provided as SEQ ID NO:3. The amino acid sequence encoded by SEQ ID NO:3 is provided as SEQ ID NO:4. A nucleotide sequence encoding an example of a codon-optimized gp120 Env gp from 93MW965.26 is provided as SEQ ID NO:5. The amino acid sequence encoded by SEQ ID NO:5 is provided as SEQ ID NO:6. A nucleotide sequence encoding an example of a codon-optimized gp120 Env gp from 92UG021.16 is provided as SEQ ID NO:7. The amino acid sequence encoded by SEQ ID NO:7 is provided as SEQ ID NO:8. A nucleotide sequence encoding an example of a codon-optimized gp120 Env gp from gp120-A/E-cons is provided as SEQ ID NO:9. The amino acid sequence encoded by SEQ ID NO:9 is provided as SEQ ID NO:10.

These non-naturally occurring sequences are shown below.

```
gp120-A-opt(92UG037.1)
                                                          (SEQ ID NO: 1)
CTGTGGGTGACCGTGTACTACGGCGTGCCCGTGTGGAAGGACGCCGAGACCACCCTGTTCTGCGCCAGCGA

CGCCAAGGCCTACGACACCGAGGTGCACAACGTGTGGGCCACCCACGCCTGCGTGCCCACCGACCCCAACC

CCCAGGAGATCTACATGGAGAACGTGACCGAGGAGTTCAACATGTGGAAGAACAACATGGTGGAGCAGATG

CACACCGACATCATCAGCCTGTGGGACCAGAGCCTGAAGCCCTGCGTGCAGCTGACCCCCCTGTGCGTGAC

CCTGGACTGCAGCTACAACATCACCAACAACATCACCAACAGCATCACCAACAGCAGCGTGAACATGCGCG

AGGAGATCAAGAACTGCAGCTTCAACATGACCACCGAGCTGCGCGACAAGAACCGCAAGGTGTACAGCCTG

TTCTACAAGCTGGACGTGGTGCAGATCAACAACGGCAACAACAGCAGCAACCTGTACCGCCTGATCAACTG

CAACACCAGCGCCCTGACCCAGGCCTGCCCCAAGGTGACCTTCGAGCCCATCCCCATCCGCTACTGCGCCC
```

-continued

CCGCCGGCTACGCCATCCTGAAGTGCAACGACAAGGAGTTCAACGGCACCGGCCTGTGCAAGAACGTGAGC

ACCGTGCAGTGCACCCACGGCATCCGCCCCGTGGTGAGCACCCAGCTGCTGCTGAACGGCAGCCTGGCCGA

GGGCAAGGTGATGATCCGCAGCGAGAACATCACCAACAACGTGAAGAACATCATCGTGCAGCTGAACGAGA

CCGTGACCATCAACTGCACCCGCCCCAACAACAACACCCGCAAGAGCGTGCGCATCGGCCCCGGCCAGACC

TTCTACGCCACCGGCGACATCATCGGCGACATCCGCCAGGCCCACTGCAACGTGAGCGGCAGCCAGTGGAA

CCGCGCCCTGCACCAGGTGGTGGGCCAGCTGCGCGAGTACTGGAACACCACCATCATCTTCAAGAACAGCA

GCGGCGGCGACCTGGAGATCACCACCCACAGCTTCAACTGCGGCGGCGAGTTCTTCTACTGCAACACCAGC

GGCCTGTTCAACAGCAACTGGACCCACAACGACACCGCCAGCATGAAGCCCAACGACACCATCACCCTGCC

CTGCCGCATCAAGCAGATCATCAACATGTGGCAGCGCGTGGGCCAGGCCATCTACGCCCCTCCCATCCAGG

GCGTGATCCGCTGCGAGAGCAACATCACCGGCCTGATCCTGACCCGCGACGGCGGCGGCAACATCAACGAG

AGCCAGATCTTCCGCCCCGGCGGCGGCGACATGCGCGACAACTGGCGCAGCGAGCTGTACAAGTACAAGGT

GGTGCGCATCGAGCCCCTGGGCGTGGCCCCCACCAAGGCCAAGCGCCGCGTGGTGGAGTAA gp120-B-opt (JR-FL)
(SEQ ID NO: 3)
GTGGAGAAGCTGTGGGTGACTGTATACTATGGGGTGCCTGTGTGGAAGGAGGCCACCACCACCCTGTTCTG

TGCCTCTGATGCCAAGGCCTATGACACTGAGGTCCACAATGTCTGGGCCACCCATGCCTGTGTGCCCACTG

ACCCCAACCCTCAGGAGGTGGTGCTGGAGAATGTGACTGAGCACTTCAACATGTGGAAGAACAACATGGTG

GAGCAGATGCAGGAGGACATCATCAGCCTGTGGGACCAGAGCCTGAAGCCCTGTGTGAAGCTGACCCCCCT

GTGTGTGACCCTGAACTGCAAGGATGTGAATGCCACCAACACCACCAATGACTCTGAGGGCACTATGGAGA

GGGGTGAGATCAAGAACTGCAGCTTCAACATCACCACCAGCATCAGGGATGAGGTGCAGAAGGAGTATGCC

CTGTTCTACAAGCTGGATGTGGTGCCCATTGACAACAACAACACCAGCTACAGGCTGATCAGCTGTGACAC

CTCTGTGATCACCCAGGCCTGCCCCAAGATCAGCTTTGAGCCCATCCCCATCCACTACTGTGCCCCTGCTG

GCTTTGCCATCCTGAAGTGCAATGACAAGACCTTCAATGGCAAAGGCCCTTGCAAGAATGTGAGCACTGTG

CAGTGCACTCATGGCATCAGGCCTGTGGTGAGCACCCAGCTGCTGCTGAATGGCAGCCTGGCTGAGGAGGA

GGTGGTGATCAGGTCTGACAACTTCACCAACAATGCCAAGACCATCATTGTGCAGCTGAAGGAGTCTGTGG

AGATCAACTGCACCAGGCCCAACAACAACACCAGGAAGAGCATTCACATTGGCCCTGGCAGGGCCTTCTAC

ACCACTGGGGAGATCATTGGGGACATCAGGCAGGCCCACTGCAACATCAGCAGGGCCAAGTGGAATGACAC

CCTGAAGCAGATTGTGATCAAGCTGAGGGAGCAGTTTGAGAACAAGACCATTGTGTTCAATCACAGCTCTG

GTGGTGATCCTGAGATTGTGATGCACAGCTTCAACTGTGGTGGTGAGTTCTTCTACTGCAACAGCACCCAG

CTGTTCAACAGCACCTGGAACAACAACACTGAGGGCAGCAACAACACTGAGGGCAACACCATCACCCTGCC

TTGCAGGATCAAGCAGATCATCAACATGTGGCAGGAGGTGGGCAAGGCCATGTATGCTCCTCCCATCAGGG

GCCAGATCAGGTGCAGCAGCAACATCACTGGCCTGCTGCTGACCAGGGATGGTGGCATCAATGAGAATGGC

ACTGAGATTTTCAGGCCTGGTGGTGGGGACATGAGGGACAACTGGAGGTCTGAGCTGTACAAGTACAAGGT

GGTGAAGATTGAGCCCCTTGGTGTGGCTCCCACCAAGGCTAAGCGCAGGGTGGTGCAGAGGGAGAAGCGCG

CTGTGTAA gp120-C-opt (93MW965.26)
(SEQ ID NO: 5)
CTGTGGGTGACCGTGTACTACGGCGTGCCCGTGTGGAAGGAGGCCAAGACCACCCTGTTCTGCGCCAGCGA

GGCCAAGGCCTACGAGAAGGAGGTGCACAACGTGTGGGCCACCCACGCCTGCGTGCCCACCGACCCCAACC

CCCAGGAGATGGTGCTGGAGAACGTGACCGAGAACTTCAACATGTGGAAGAACGACATGGTGAACCAGATG

CACGAGGACATCATCAGCCTGTGGGACCAGAGCCTGAAGCCCTGCGTGAAGCTGACCCCCCTGTGCGTGAC

CCTGAACTGCACCAACGCCAACGGCACCAACAATAACGGCACCGTGAACGTGAACGACACCATGTACGGCG

-continued

AGATCAAGAACTGCAGCTTCAACATGACCACCGAGCTGCGGGACAAGAAGAAGCAGGTGTACGCCCTGTTC

TACAAGCTGGACATCGTGAGCCTGAACGAGAACAGCAACAACAGCAGCGAGTACCGGCTGATCAACTGCAA

CACCAGCGTGATCACCCAGGCCTGCCCCAAGGTGACCTTCGACCCCATCCCCATCCACTACTGCGCCCCTG

CCGGCTACGCCATCCTGAAGTGCAACAACAAGACCTTCACCGGCATCGGCCCCTGCAAGAACGTGAGCACC

GTGCAGTGCACCCACGGCATCAAGCCCGTGGTGAGCACCCAGCTGCTGCTGAACGGCAGCCTGGCCGAGGA

GGAGATCATCGTGCGGAGCGAGAACCTGACCGACAACGTGAAAACCATCATCGTGCACCTGAATGAGAGCG

TGGAGATCGTGTGCACCAGGCCCAACAACAACACCCGGAAGAGCGTGCGGATCGGCCCTGGCCAGACCTTC

TACGCCACCGGCGCCATCATCGGCGACATCCGGCAGGCCCACTGCAACATCAGCACCATCAAGTGGAACAA

GACCCTGCAGGGCGTGGAGAAGAAGCTGAAGGAGCACTTCCCCAACAAGACCATCGAGTTCAAGCCCAGCA

GCGGCGGAGACCTGGAGATCACCACCCACAGCTTCAACTGCAGGGGCGAGTTCTTCTGCTGCAACACCTCC

AACCTGTTCACCAGCAATCTGTTCACCGACAACCTGACCAACACCACCAACATCACCCTGCCCTGCCGGAT

CAAGCAGATCATCAACATGTGGCAGGGCGTGGGCAGGGCCATGTACGCCCCTCCCATCGCCGGCAACATCA

CCTGCAAGAGCAACATCACCGGCCTGCTGCTGACCCGGGACGGCGGCGAGAACAACCGGACCGAGACCTTC

AGGCCCGGAGGCGGCGACATGAAGGACAACTGGCGGAGCGAGCTGTACAAGTACAAGGTGGTGGAGATCAA

GCCCCTGGGCGTGGCCCCCACCGGCGCCAAGCGCCGCGTGGTGGAGTAA gp120-D-opt (92UG021.16)

(SEQ ID NO: 7)
CTGTGGGTGACCGTGTACTACGGCGTGCCCGTGTGGAAGGAGGCCACCACCACCCTGTTCTGCGCCAGCGA

CGCCAAGAGCTACGAGGCCGAGGCCCACAACATCTGGGCCACCCACGCCTGCGTGCCCACCGACCCCAACC

CCCAGGAGATCGTGCTGGAGAACGTGACCGAGAACTTCAACATCTGGAAGAACAACATGGTGGAGCAGATG

CACGACGACATCATCAGCCTGTGGGACCAGAGCATCAAGCCCTGCGTGAAGCTGACCCCCCTGTGCGTGAC

CCTGAACTGCACCGAGTGGAAGAACGCCACCACAAACGCCACCAACGAGGGCATCGGCATGAAGAACTGCA

GCTTCACCGAGGTGCGGGACAAGAAGAAGCAGGCCTACGCCCTGTTCTACAAGCTGGACGTGGTGCAGATG

AACGACGATAACAGCACCAACACCAGCTACCGGCTGATCAACTGCAACGCCAGCACCATCACCCAGGCCTG

CCCCAAGATCAGCTTCGAGCCCATCCCCATCCACTACTGCGCCCCTGCCGGCTTCGCCATCCTGAAGTGCA

ACGACAAGAAGTTCAACGGCACCGGCCCCTGCAAGAACGTGAGCACCGTGCAGTGCACCCACGGCATCAAG

CCCGTGGTGAGCACCCAGCTGCTGCTGAACGGCAGCCTGGCCGAGGAGGAGATCATCATCCGGAGCAAGAA

CCTGACCAACAACGCCAAGATCATCATCGTGCACCTGAACGAGAGCGTGCCCATCAACTGCACCCGGCCCT

ACGACAAGGTGAGCTACCGGACCCCCATCGGCGTGGGCAGGGCCAGCTACACCACCCGGATCAAGGGCGAC

ATCCGGCAGGCCCACTGCAACATCAGCGGCGAGAAGTGGAACAAGACCCTGCAGCAGGTGGCCGTGAAGCT

GCGGGACCTGCTGAACCAGACCGCCATCATCTTCAAGCCCAGCAGCGGCGGAGACCCCGAGATCACCACCC

ACAGCTTCAACTGTGGCGGCGAGTTCTTCTACTGCAACACCAGCGGCCTGTTCAACAACAGCGTGTGGACC

AGCAACAGCACCATCGGCGCCAACGGCACCATCACCCTGCCCTGCAGGATCAAGCAGATCATCAACATGTG

GCAGGGCGTGGGCAAGGCCATGTACGCCCCTCCCATCGAGGGCCAGATCAACTGCAGCTCCACCATCACCG

GCCTGCTGCTGACCCGGGACGGCGGCGTGAAGAACAACAGCCAGAACGAGACCTTCAGGCCCGGAGGCGGC

GACATGCGGGACAACTGGCGGAACGAGCTGTACAAGTACAAGGTGGTGCGGATCGAGCCCCTGGGCCTGGC

CCCCACCAAGGCCAAGCGCCGCGTGGTGGAGTAA gp120-A/E-opt (gp120-A/E-cons)

(SEQ ID NO: 9)
CTGTGGGTCACCGTGTACTACGGCGTGCCCGTGTGGCGGGACGCCGATACCACCCTGTTCTGTGCCAGCGA

CGCCAAGGCCCACGAGACAGAGGTGCACAACGTGTGGGCCACCCACGCCTGCGTGCCCACCGACCCCAACC

CCCAGGAAATCCACCTGGAAAACGTGACCGAGAACTTCAACATGTGGAAGAACAACATGGTCGAGCAGATG

CAGGAAGATGTCATCAGCCTCTGGGACCAGAGCCTGAAGCCCTGCGTGAAGCTGACCCCCCTGTGCGTGAC

-continued

```
CCTGAACTGCACCAACGCCAACCTGACCAACAACAACATCAACGGCAGCAACATCATCGGCAACATCACCG

ACGAAGTGCGGAACTGCTCCTTCAACATGACCACCGAGCTGCGGGACAAGAAACAGAAGGTGCACGCCCTG

TTCTACAAGCTGGACATCGTGCAGATCGAGGACAACAGCAACAGCAGCGAGTACCGGCTGATCAACTGCAA

CACCAGCGTGATCAAGCAGGCCTGCCCCAAGATCAGCTTCGACCCCATCCCCATCCACTACTGCACCCCTG

CCGGCTACGCCATCCTGAAGTGCAACGACAAGAACTTCAATGGCACCGGCCCTGCAAGAACGTGTCCAGC

GTGCAGTGCACCCACGGCATCAAGCCCGTGGTGTCCACCCAGCTGCTGCTGAATGGCAGCCTGGCCGAGGA

AGAGATCATCATCAGAAGCGAGAACCTCACCAACAATGCCAAGACCATCATCGTGCACCTGAACAAGAGCG

TGGAAATCAACTGCACCCGGCCCAGCAACAACACCCGGACCAGCATCACCATCGGCCCTGGCCAGGTGTTC

TACCGGACCGGCGATATCATCGGCGATATCCGGAAGGCCTACTGCGAGATCAACGGCACCAAGTGGAACGA

GGTGCTGAAGCAGGTCACAGGCAAGCTGAAAGAGCACTTCAACAACAAGACAATCATCTTCCAGCCCCCT

CTGGCGGCGACCTGGAAATCACCATGCACCACTTCAACTGTCGGGCGAGTTCTTCTACTGCAATACCACC

AAGCTGTTCAACAATACCTGCATCGGCAACGAGACAATGGAAGGCTGCAATGGCACCATCATCCTGCCCTG

CAAGATCAAGCAGATCATCAATATGTGGCAGGGCGTGGGCCAGGCTATGTACGCCCCTCCCATCAGCGGCC

GGATCAACTGCGTGTCCAATATCACCGGCATCCTGCTGACCCGGACGGCGGAGCCAACAACACCGCCAAC

GAGACATTCAGACCCGGCGGAGGCAACATCAAGGACAACTGGCGGAGCGAGCTGTACAAGTACAAGGTGGT

GCAGATTGAGCCCCTGGGAATCGCCCCCACCCGGGCCAAGCGGAGAGTGGTGGAATGATGA
```

Construction of Codon-Optimized Sequences

Viral proteins and proteins that are naturally expressed at low levels can provide challenges for efficient expression by recombinant means. In addition, viral proteins often display a codon usage that is inefficiently translated in a host cell (e.g., a mammalian or avian host cell). Alteration of the codons native to the viral sequence can facilitate more robust expression of these proteins. Codon preferences for abundantly expressed proteins have been determined in a number of species, and can provide guidelines for codon substitution. Synthesis of codon-optimized sequences can be achieved by substitution of viral codons in cloned sequences, e.g., by site-directed mutagenesis, or by construction of oligonucleotides corresponding to the optimized sequence by chemical synthesis. See, e.g., Mirzabekov et al., J. Biol. Chem., 274(40):28745-50, 1999.

Codon-optimization should also include consideration of other factors such as the efficiency with which the sequence can be synthesized in vitro (e.g., as oligonucleotide segments) and the presence of other features that affect expression of the nucleic acid in a cell. For example, sequences that result in RNAs predicted to have a high degree of secondary structure should be avoided. AT- and GC-rich sequences that interfere with DNA synthesis should also be avoided. Other motifs that can be detrimental to expression include internal TATA boxes, chi-sites, ribosomal entry sites, procarya inhibitory motifs, cryptic splice donor and acceptor sites, and branch points. These features can be identified manually or by computer software and they can be excluded from the optimized sequences.

An HIV polypeptide (e.g., gp120) or antigenic fragment thereof encoded by a codon-optimized nucleic acid is any polypeptide sharing an epitope with a naturally occurring HIV polypeptide, e.g., gp120. The gp120 polypeptides provided herein can differ from a wild type sequence by additions or substitutions within the amino acid sequence, and may preserve a biological function of the influenza polypeptide (e.g., receptor binding). Amino acid substitutions may be made on the basis of similarity in polarity, charge, solubility, hydrophobicity, hydrophilicity, and/or the amphipathic nature of the residues involved.

Nonpolar (hydrophobic) amino acids include alanine, leucine, isoleucine, valine, proline, phenylalanine, tryptophan, and methionine. Polar neutral amino acids include glycine, serine, threonine, cysteine, tyrosine, asparagine, and glutamine. Positively charged (basic) amino acids include arginine, lysine, and histidine. Negatively charged (acidic) amino acids include aspartic acid and glutamic acid. Alterations of residues are preferably conservative alterations, e.g., a basic amino acid is replaced by a different basic amino acid, as described herein.

A nucleic acid that is codon-optimized for expression in mammalian cells can be expressed in mammalian cells using a mammalian expression vector. Examples of mammalian expression vectors include pCDM8 (Seed, *Nature* 329:840, 1987) and pMT2PC (Kaufman et al., *EMBO J.* 6:187-195, 1987). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see, e.g., Chapters 16 and 17 of Sambrook, J., Fritsh, E. F., and Maniatis, T., *Molecular Cloning: A Laboratory Manual.,* 2nd ed., Cold Spring Harbor Laboratory, Cold Spring Harbor Laboratory Press, Cold Spring Harbor, N.Y., 1989.

Nucleic acid molecules described herein include both RNA and DNA, including genomic DNA and synthetic (e.g., chemically synthesized) DNA. Nucleic acids can be double-stranded or single-stranded. Where single-stranded, the nucleic acid can be a sense strand or an antisense strand. Nucleic acid molecules can be synthesized using oligonucleotide analogs or derivatives (e.g., inosine or phosphorothioate nucleotides). Such oligonucleotides can be used, for example, to prepare nucleic acid molecules that have altered base-pairing abilities or increased resistance to nucleases.

The term "isolated nucleic acid" means a nucleic acid, e.g., DNA or RNA, that is not immediately contiguous with both of the coding sequences with which it is immediately contiguous (one on the 5' end and one on the 3' end) in the naturally occurring genome of the organism from which it is derived. Thus, in one embodiment, an isolated or synthetic nucleic acid includes some or all of the 5' non-coding (e.g., promoter) sequences that are immediately contiguous to the nucleic acid coding sequence. The term includes, for example, recombinant DNA that is incorporated into a vector, into an autonomously replicating plasmid or virus, or into the genomic DNA of a prokaryote or eukaryote, or which exists as a separate molecule (e.g., a genomic DNA fragment produced by PCR or restriction endonuclease treatment) independent of other sequences. It also includes a recombinant DNA that is part of a hybrid gene encoding an additional polypeptide sequence.

The invention includes vectors, preferably expression vectors, containing a nucleic acid that encodes the polypeptides described herein. As used herein, the term "vector" refers to a nucleic acid molecule capable of transporting another nucleic acid to which it has been linked and can include, e.g., a plasmid, cosmid, or viral vector. The vector can autonomously replicate or it can integrate into a host cell's DNA. Viral vectors include, e.g., replication-defective retroviruses, adenoviruses, and adeno-associated viruses.

A vector can include a nucleic acid in a form suitable for expression of the nucleic acid in a host cell. Preferably a recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce Env gps encoded by nucleic acids as described herein.

The recombinant expression vectors of the invention can be designed for expression of polypeptides in prokaryotic or eukaryotic cells. For example, polypeptides of the invention can be expressed in $E.$ $coli$, insect cells (e.g., using baculovirus expression vectors), yeast cells, or mammalian cells (e.g., CHO or COS cells). Suitable host cells are discussed further in Goeddel, (1990) Gene Expression Technology: Methods in Enzymology 185, Academic Press, San Diego, Calif. Alternatively, the recombinant expression vector can be transcribed and translated in vitro, for example using T7 promoter regulatory sequences and T7 polymerase.

In one embodiment, the HIV envelope glycoproteins described herein can be expressed in mammalian cells, e.g., CHO cells, and harvested and/or purified in the presence of a divalent metal ion to precipitate contaminating proteins, including enzymes such as fucosidase. For example, a divalent metal ion such as $Zn^{2+}$, $Cu^{2+}$, $Co^{2+}$, $Ni^{2+}$, or $Ca^{2+}$ is added to the culture medium in an amount effective to precipitate unwanted proteins. Preferably, the divalent metal ion is added in the form of a salt, e.g., a divalent metal ion salt such as $ZnCl_2$, $CuSO_4$, $CoSO_4$, $NiSO_4$, and $CaCl_2$. Generally, the amount of divalent metal ion that should be added to a crude protein preparation depends on the nature of the divalent metal ion and the components to be removed. One of skill in the art will be able to adjust the final optimum concentration as a function of these specific parameters. Nonetheless, contaminating proteins present in the crude preparation will generally precipitate once the divalent metal ion is added to a final concentration of not less than 10 mM, e.g., not less than 20 mM, not less than 40 mM, not less than 60 mM, or not less than 80 mM. Although it is possible to add the divalent metal ion in bulk, it is generally not necessary to exceed a final concentration of about 100 to 120 mM. Other details of a suitable countercurrent extractor and methods are described in U.S. Pat. No. 5,276,141, the entire contents of which are hereby incorporated by reference.

Expression of proteins in prokaryotes is most often carried out in $E.$ $coli$ with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, Gene 67:31-40, 1988), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

One can maximize recombinant protein expression in $E.$ $coli$ by expressing the protein in host bacteria with an impaired capacity to proteolytically cleave the recombinant protein (Gottesman (1990) Gene Expression Technology: Methods in Enzymology 185:119-128, Academic Press, San Diego, Calif.). Another strategy is to alter the nucleic acid sequence of the nucleic acid to be inserted into an expression vector so that the individual codons for each amino acid are those preferentially utilized in $E.$ $coli$ (Wada et al., Nucleic Acids Res 20:2111-2118, 1992). Such alteration of nucleic acid sequences of the invention can be carried out by standard DNA synthesis techniques.

The term "purified" refers to a nucleic acid or polypeptide that is substantially free of cellular or viral material with which it is naturally associated, or culture medium (when produced by recombinant DNA techniques), or chemical precursors or other chemicals (when chemically synthesized). Moreover, an isolated or synthetic, codon-optimized nucleic acid molecule is a nucleic acid molecule that is not naturally occurring and would not be found in the natural state.

In some embodiments, the invention includes nucleic acid molecules with a nucleotide sequence that is substantially identical to the nucleotide sequence of SEQ ID NO:1, 3, 5, 7, or 9. A nucleic acid sequence that is "substantially identical" to SEQ ID NO:1, 3, 5, 7, or 9 has at least 90% identity, e.g., at least about 92%, 95%, 96%, 97%, 98%, 99%, or identical) to a nucleotide sequence represented by SEQ ID NO:1, 3, 5, 7, or 9. For purposes of comparison of nucleic acids, the length of the reference nucleic acid sequence will be at least 50 nucleotides, but can be longer, e.g., at least 60 or more nucleotides or the entire length of the reference sequence.

To determine the percent identity of two amino acid or nucleic acid sequences, the sequences are aligned for optimal comparison purposes (i.e., gaps can be introduced as required in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of overlapping positions×100). The two sequences may be of the same length.

The percent identity or homology between two sequences can be determined using a mathematical algorithm. A non-limiting example of a mathematical algorithm utilized for the comparison of two sequences is the algorithm of Karlin and Altschul, Proc. Natl. Acad. Sci. USA 87:2264-2268, 1990, modified as in Karlin and Altschul, Proc. Natl. Acad. Sci. USA 90:5873-5877, 1993. Such an algorithm is incorporated into the NBLAST and XBLAST programs of Altschul et al., J Mol Biol 215:403-410, 1990. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to polypeptide molecules of the invention. To obtain gapped alignments for comparison purposes, Gapped BLAST can be utilized as described in Altschul et al., Nucleic Acids Res. 25:3389-3402, 1997. When utilizing BLAST and Gapped BLAST programs, the default parameters of the respective programs (e.g., XBLAST and NBLAST) can be used. See online at ncbi.nlm.nih.gov.

In other embodiments, the invention includes variants, homologs, and/or fragments of the nucleotide sequences represented by SEQ ID NO:1, 3, 5, 7, and 9. The terms "variant" or "homolog" in relation to nucleic acids include any substitution, variation, modification, replacement, deletion, or addition of one (or more) nucleotides from or to the sequence of a nucleic acid molecule.

"Substantial homology" or "substantially homologous," where homology indicates sequence identity, means at least 90% identical (e.g., at least about 92%, 95%, 96%, 97%, 98%, or 99%) sequence identity, as judged by direct sequence alignment and comparison. The term "homology" as used herein can be equated with the term "identity." "Substantial homology" when assessed by the BLAST algorithm equates to sequences which match with an EXPECT value of at least about 7, e.g., at least about 9, 10, or more. The default threshold for EXPECT in BLAST searching is usually 10.

The invention also includes nucleic acid molecules that hybridize, e.g., under stringent hybridization conditions (as defined herein) to all or a portion of the nucleotide sequences represented by SEQ ID NO:1, 3, 5, 7, 9, or a complement thereof. The hybridizing portion of the hybridizing nucleic acids is typically at least 15 (e.g., 20, 30, or 50) nucleotides in length. The hybridizing portion of the hybridizing nucleic acid is at least about 75%, e.g., at least about 80%, 95%, 96%, 97%, 98%, 99%, or 100%, identical to the sequence of a portion or all of a nucleic acid encoding an Env gps polypeptide, or to its complement. Hybridizing nucleic acids of the type described herein can be used as a cloning probe, a primer (e.g., a PCR primer), or a diagnostic probe. Nucleic acid molecules that hybridize to the nucleotide sequence represented by SEQ ID NO:1, 3, 5, 7, or 9, are considered "antisense oligonucleotides."

High stringency conditions are hybridizing at 68° C. in 5×SSC/5×Denhardt's solution/1.0% SDS, or in 0.5 M NaHPO4 (pH 7.2)/1 mM EDTA/7% SDS, or in 50% formamide/0.25 M NaHPO4 (pH 7.2)/0.25 M NaCl/1 mM EDTA/7% SDS; and washing in 0.2×SSC/0.1% SDS at room temperature or at 42° C., or in 0.1×SSC/0.1% SDS at 68° C., or in 40 mM NaHPO4 (pH 7.2)/1 mM EDTA/5% SDS at 50° C., or in 40 mM NaHPO4 (pH 7.2) 1 mM EDTA/1% SDS at 50° C. Stringent conditions include washing in 3×SSC at 42° C. The parameters of salt concentration and temperature can be varied to achieve the optimal level of identity between the probe and the target nucleic acid. Additional guidance regarding such conditions is available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

Also included in the invention are genetic constructs (e.g., vectors and plasmids) that include a nucleic acid described herein, operably linked to a transcription and/or translation sequence to enable expression, e.g., expression vectors. A selected nucleic acid, e.g., a DNA molecule encoding an Env gps polypeptide, is "operably linked" to another nucleic acid molecule, e.g., a promoter, when it is positioned either adjacent to the other molecule or in the same or other location such that the other molecule can control transcription and/or translation of the selected nucleic acid.

Also included in the invention are various engineered cells, e.g., transformed host cells, which contain a nucleic acid molecule described herein. A transformed cell is a cell into which (or into an ancestor of which) has been introduced, by means of recombinant DNA techniques, a nucleic acid encoding an Env gps polypeptide. Both prokaryotic and eukaryotic cells are included. Mammalian cells can include host cells for an attaching enteric organism, e.g., intestinal cells, HeLa cells, and mouse embryonic fibroblasts. Prokaryotic cells can include bacteria, e.g., *Escherichia coli*. An engineered cell exemplary of the type included in the invention is an *E. coli* strain that expresses an Env gps.

Nucleic Acid Compositions

Nucleic acid compositions that encode antigens of primary HIV isolates are also provided. In some embodiments, the compositions include one, two, or more, e.g., three or more, four or more, or all five synthetic, codon-optimized nucleic acid molecules from the group consisting of synthetic nucleic acid molecules comprising nucleotide sequences that have at least or about 90%, e.g., at least or about 92%, 95%, 96%, 97%, 98%, 99%, or 100%, identity to the nucleotide sequence of SEQ ID NOs:1, 3, 5, 7, and 9. For example, nucleic acid compositions can include or consist of nucleic acid molecules comprising or consisting of a nucleotide sequence that has at least or about 90% identity to the nucleotide sequence of SEQ ID NOs:1 and 3; SEQ ID NOs:1, 3, and 5; SEQ ID NOs:1, 3, 5, and 7; SEQ ID NOs:3, 5, 7, and 9; SEQ ID NOs:5, 7, and 9; SEQ ID NOs:1, 3, 5, and 9; SEQ ID NOs:1, 3, 7, and 9; SEQ ID NOs:1, 5, 7, and 9; SEQ ID NOs:1 and 9; SEQ ID NOs:3 and 9; SEQ ID NOs:5 and 9; or SEQ ID NOs:7 and 9.

There are many ways of presenting nucleic acid encoding antigen to a host. DNA vaccines can consist of naked DNA plasmid encoding the antigen. Bacterial vectors, replicon vectors, live attenuated bacteria, DNA vaccine co-delivery with live attenuated vectors, and viral vectors for expression of heterologous genes also can be used. Bacterial vectors such as BCG and *Listeria* can also be used. In the case of naked DNA replicon vectors, a mammalian expression plasmid serves as a vehicle for the initial transcription of the replicon. The replicon is amplified within the cytoplasm, resulting in more abundant mRNA encoding the heterologous gene such that initial transfection efficiency may be less important for immunogenicity. Live attenuated viral vectors (e.g., recombinant vaccinia (e.g., modified vaccinia Ankara (MVA), IDT Germany), recombinant adenovirus, avian poxvirus (e.g., canarypox (e.g., ALVAC®, Aventis Pasteur) or fowlpox), poliovirus, and alphavirus virion vectors) have been successful in inducing cell-mediated immune response and can be used as well. The avian poxviruses are defective in mammalian hosts, but can express inserted heterologous genes under early promoters. Recombinant adenovirus and poliovirus vectors can thrive in the gut and so can stimulate efficient mucosal immune responses. Finally, attenuated bacteria can also be used as a vehicle for DNA vaccine delivery. Examples of suitable bacteria include *S. enterica, S. tymphimurium, Listeria*, and BCG. The use of mutant bacteria with weak cell walls can aid the exit of DNA plasmids from the bacterium.

DNA uptake can sometimes be improved by the use of the appropriate adjuvants. Synthetic polymers (e.g., polyamino acids, co-polymers of amino acids, saponin, paraffin oil, muramyl dipeptide, Regressin (Vetrepharm, Athens Ga.), and Avridine) and liposomal formulations can be added as adjuvants to the vaccine formulation to improve DNA stability and DNA uptake by the host cells, and may decrease the dosage required to induce an effective immune response. Regardless of route, adjuvants can be administered before, during, or after administration of the nucleic acid. Not only can the adjuvant increase the uptake of nucleic acid into host cells, it can increase the expression of the antigen from the nucleic acid within the cell, induce antigen presenting cells to infiltrate the region of tissue where the antigen is being expressed, or increase the antigen-specific response provided by lymphocytes.

Nucleic acid uptake can be improved in other ways as well. For example, DNA uptake via IM delivery of vaccine can be improved by the addition of sodium phosphate to the formulation. Increased DNA uptake via IM delivery can also be accomplished by electrotransfer (e.g., applying a series of electrical impulses to muscle immediately after DNA immunization). Adjuvants which can also be added to the vaccine to improve DNA stability and uptake as well as improve immune induction include water emulsions (e.g., complete and incomplete Freund's adjuvant), oil, *Corynebacterium parvum, Bacillus Calmette Guerin*, iron oxide, sodium alginate, aluminum hydroxide, aluminum and calcium salts (i.e., alum), unmethylated CpG motifs, glucan, and dextran sulfate. Coinjection of cytokines, ubiquitin, or costimulatory molecules can also help improve immune induction. The antigens described herein can also be fused with cytokine genes, helper epitopes, ubiquitin, or signal sequences to enhance an immune response. Fusions can also be used to aid in targeting to certain cell types.

The medium in which the DNA vector is introduced should be physiologically acceptable for safety reasons. Suitable pharmaceutical carriers include sterile water, saline, dextrose, glucose, or other buffered solutions (e.g., phosphate buffered saline). Included in the medium can be physiologically acceptable preservatives, stabilizers, diluents, emulsifying agents, pH buffering agents, viscosity enhancing agents, colors, etc.

Once the DNA vaccine is delivered, the nucleic acid molecules (e.g., DNA plasmids) are taken up into host cells, which then express the plasmid DNA as protein. Once expressed, the protein is processed and presented in the context of self-major histocompatibility (MHC) class I and class II molecules. The host then develops an immune response against the DNA-encoded immunogen. To improve the effectiveness of the vaccine, multiple injections can be used for therapy or prophylaxis over extended periods of time. To improve immune induction, a prime-boost strategy can be employed. Priming vaccination with DNA and a different modality for boosting (e.g., live viral vector or protein antigen) has been successful in inducing cell-mediated immunity. The timing between priming and boosting varies and is adjusted for each vaccine.

Administration of Nucleic Acid Vaccines

The nucleic acid compositions described herein can be administered, or inoculated, to an individual as naked nucleic acid molecules (e.g., naked DNA plasmid) in physiologically compatible solution such as water, saline, Tris-EDTA (TE) buffer, or in phosphate buffered saline (PBS). They can also be administered in the presence of substances (e.g., facilitating agents and adjuvants) that have the capability of promoting nucleic acid uptake or recruiting immune system cells to the site of inoculation. Adjuvants are described elsewhere herein. Vaccines have many modes and routes of administration. They can be administered intradermally (ID), intramuscularly (IM), and by either route, they can be administered by needle injection, gene gun, or needleless jet injection (e.g., Biojector™ (Bioject Inc., Portland, Oreg.). Other modes of administration include oral, intravenous, intraperitoneal, intrapulmonary, intravitreal, and subcutaneous inoculation. Topical inoculation is also possible, and can be referred to as mucosal vaccination. These include intranasal, ocular, oral, vaginal, or rectal topical routes. Delivery by these topical routes can be by nose drops, eye drops, inhalants, suppositories, or microspheres.

Conventional particle bombardment can be used to deliver nucleic acids that express Env gps polypeptides into skin or onto mucosal surfaces, e.g., using commercial devices. For example, the ACCELL II® (POWDERJECT® Vaccines, Inc., Middleton, Wis.) particle bombardment device, one of several commercially available "gene guns," can be employed to deliver nucleic acid-coated gold beads. HELIOS GENE GUN® (Bio-Rad) can also be used to administer the DNA particles. Information on particle bombardment devices and methods can be found in sources including the following: Yang et al., *Proc. Natl. Acad. Sci. USA*, 87:9568, 1990; Yang, *CRC Crit. Rev. Biotechnol.*, 12:335, 1992; Richmond et al., *Virology* 230:265-274, 1997; Mustafa et al., *Virology* 229:269-278, 1997; Livingston et al., *Infect. Immun.*, 66:322-329, 1998; and Cheng et al., *Proc. Natl. Acad. Sci. USA*, 90:4455, 1993.

In some embodiments, an individual is inoculated by a mucosal route. The codon-optimized nucleic acids or compositions can be administered to a mucosal surface by a variety of methods including nucleic acid-containing nose-drops, inhalants, suppositories, or microspheres. Alternatively, nucleic acid vectors containing the codon-optimized nucleic acids can be encapsulated in poly(lactide-co-glycolide) (PLG) microparticles by a solvent extraction technique, such as the ones described in Jones et al., *Infect. Immun.*, 64:489, 1996; and Jones et al., *Vaccine*, 15:814, 1997. For example, the nucleic acids can be emulsified with PLG dissolved in dichloromethane, and this water-in-oil emulsion is emulsified with aqueous polyvinyl alcohol (an emulsion stabilizer) to form a (water-in-oil)-in-water double emulsion. This double emulsion is added to a large quantity of water to dissipate the dichloromethane, which results in the microdroplets hardening to form microparticles. These microdroplets or microparticles are harvested by centrifugation, washed several times to remove the polyvinyl alcohol and residual solvent, and finally lyophilized. The microparticles containing nucleic acid have a mean diameter of 0.5 µm.

To test for nucleic acid content, the microparticles are dissolved in 0.1 M NaOH at 100° C. for 10 minutes. The $A_{260}$ is measured, and the amount of nucleic acid calculated from a standard curve. Incorporation of nucleic acid into microparticles is in the range of 1.76 g to 2.7 g nucleic acid per milligram PLG. Microparticles containing about 1 to 100 µg of nucleic acid are suspended in about 0.1 to 1 ml of 0.1 M sodium bicarbonate, pH 8.5, and orally administered to mice or humans.

Regardless of the route of administration, an adjuvant can be administered before, during, or after administration of the codon-optimized nucleic acid molecules encoding an Env gps polypeptide. An adjuvant can increase the uptake of the nucleic acid into the cells, increase the expression of the polypeptide from the nucleic acid within the cell, induce antigen presenting cells to infiltrate the region of tissue where the polypeptide is being expressed, or increase the antigen-specific response provided by lymphocytes.

Suitable doses of nucleic acid compositions for humans can range from 1 μg/kg to 1 mg/kg of total nucleic acid, e.g., from 5 μg/kg-500 mg/kg of total DNA, 10 μg/kg-250 μg/kg of total DNA, or 10 μg/kg-170 μg/kg of total DNA. In one embodiment, a human subject (18-50 years of age, 45-75 kg) is administered 1.2 mg-7.2 mg of DNA. "Total DNA" and "total nucleic acid" refers to a pool of nucleic acids encoding distinct antigens. For example, a dose of 50 mg of total DNA encoding 5 different Env antigens can have 1 mg of each antigen. DNA vaccines can be administered multiple times, e.g., between two to six times, e.g., three, four, or five times. In an exemplary method, 100 μg of a DNA composition is administered to a human subject at 0, 4, and 12 weeks (100 μg per administration).

Polypeptide Compositions

Polypeptides or proteins, e.g., isolated and purified polypeptides, encoding antigens of primary HIV isolates can be administered individually or as "boosts" before, at the same time as, or after vaccination with nucleic acid compositions. Polypeptide compositions can be administered multiple times, e.g., between two to six times, e.g., three, four, or five times. In one embodiment, the nucleic acid composition is administered three times before the polypeptide composition is administered two times. Recombinant proteins (e.g., proteins produced by cloning DNA encoding antigens of primary isolates using standard molecular biological techniques) can be one source of isolated proteins for boosting. Proteins used for boosting an individual can include the same sequences as encoded by the DNA vaccines previously administered to the individual, e.g., gp120.

In some embodiments, the isolated Env gps polypeptides described herein are encoded by a codon-optimized nucleotide sequence, e.g., a nucleic acid molecule comprising a nucleotide sequence that has at least or about 90%, e.g., at least or about 92%, 95%, 96%, 97%, 98%, 99%, or 100%, identity to all or portions of the sequence of SEQ ID NO:1, 3, 5, 7, or 9. Polypeptides substantially identical to the Env gps polypeptide sequences described herein have an amino acid sequence that has at least or about 90%, e.g., at least about 92%, 95%, 96%, 97%, 98%, 99%, or 100%, identity to all or portions of the amino acid sequences of the polypeptides represented by SEQ ID NO:2, 4, 6, 8, 10, 11, 12, 13, or 14 (listed below), wherein the present identity is measured as described herein. For purposes of comparison, the length of the reference polypeptide sequence is at least 50 amino acids, e.g., at least 60 or 80 amino acids, or the entire length of the reference polypeptide.

```
gp120-A(92UG037.1)
                                                            (SEQ ID NO: 2)
LWVTVYYGVPVWKDAETTLFCASDAKAYDTEVHNVWATHACVPTDPNPQEIYMENVTEEFNMWKNNMVEQM

HTDIISLWDQSLKPCVQLTPLCVTLDCSYNITNNITNSITNSSVNMREEIKNCSFNMTTELRDKNRKVYSL

FYKLDVVQINNGNNSSNLYRLINCNTSALTQACPKVTFEPIPIRYCAPAGYAILKCNDKEFNGTGLCKNVS

TVQCTHGIRPVVSTQLLLNGSLAEGKVMIRSENITNNVKNIIVQLNETVTINCTRPNNNTRKSVRIGPGQT

FYATGDIIGDIRQAHCNVSGSQWNRALHQVVGQLREYWNTTIIFKNSSGGDLEITTHSFNCGGEFFYCNTS

GLFNSNWTHNDTASMKPNDTITLPCRIKQIINMWQRVGQAIYAPPIQGVIRCESNITGLILTRDGGGNINE

SQIFRPGGGDMRDNWRSELYKYKVVRIEPLGVAPTKAKRRVVE gp120-B (JR-FL)
                                                            (SEQ ID NO: 4)
VEKLWVTVYYGVPVWKEATTTLFCASDAKAYDTEVHNVWATHACVPTDPNPQEVVLENVTEHFNMWKNNMV

EQMQEDIISLWDQSLKPCVKLTPLCVTLNCKDVNATNTTNDSEGTMERGEIKNCSFNITTSIRDEVQKEYA

LFYKLDVVPIDNNNTSYRLISCDTSVITQACPKISFEPIPIHYCAPAGFAILKCNDKTFNGKGPCKNVSTV

QCTHGIRPVVSTQLLLNGSLAEEEVVIRSDNFTNNAKTIIVQLKESVEINCTRPNNNTRKSIHIGPGRAFY

TTGETIGDIRQAHCNISRAKWNDTLKQIVIKLREQFENKTIVFNHSSGGDPEIVMHSFNCGGEFFYCNSTQ

LFNSTWNNNTEGSNNTEGNTITLPCRIKQIINMWQEVGKAMYAPPIRGQIRCSSNITGLLLTRDGGINENG

TEIFRPGGGDMRDNWRSELYKYKVVKIEPLGVAPTKAKRRVVQREKRAV
```

-continued gp120-C(93MW965.26)
(SEQ ID NO: 6)
LWVTVYYGVPVWKEAKTTLFCASEAKAYEKEVHNVWATHACVPTDPNPQEMVLENVTENFNMWKNDMVNQM

HEDIISLWDQSLKPCVKLTPLCVTLNCTNANGTNNNGTVNVNDTMYGEIKNCSFNMTTELRDKKKQVYALF

YKLDIVSLNENSNNSSEYRLINCNTSVITQACPKVTFDPIPIHYCAPAGYAILKCNNKTFTGIGPCKNVST

VQCTHGIKPVVSTQLLLNGSLAEEETIVRSENLTDNVKTIIVHLNESVEIVCTRPNNNTRKSVRIGPGQTF

YATGAIIGDIRQAHCNISTIKWNKTLQGVEKKLKEHFPNKTIEFKPSSGGDLEITTHSFNCRGEFFCCNTS

NLFTSNLFTDNLTNTTNITLPCRIKQIINMWQGVGRAMYAPPIAGNITCKSNITGLLLTRDGGENNRTETF

RPGGGDMKDNWRSELYKYKVVEIKPLGVAPTGAKRRVVE gp120-D(92UG021.16)
(SEQ ID NO: 8)
LWVTVYYGVPVWKEATTTLFCASDAKSYEAEAHNIWATHACVPTDPNPQEIVLENVTENFNIWKNNMVEQM

HDDIISLWDQSIKPCVKLTPLCVTLNCTEWKNATTNATNEGIGMKNCSFTEVRDKKKQAYALFYKLDVVQM

NDDNSTNTSYRLINCNASTITQACPKISFEPIPIHYCAPAGFAILKCNDKKFNGTGPCKNVSTVQCTHGIK

PVVSTQLLLNGSLAEEEIIIRSKNLTNNAKIIIVHLNESVPINCTRPYDKVSYRTPIGVGRASYTTRIKGD

IRQAHCNISGEKWNKTLQQVAVKLRDLLNQTAIIFKPSSGGDPEITTHSFNCGGEFFYCNTSGLFNNSVWT

SNSTIGANGTITLPCRIKQIINMWQGVGKAMYAPPIEGQINCSSTITGLLLTRDGGVKNNSQNETFRPGGG

DMRDNWRNELYKYKVVRIEPLGLAPTKAKRRVVE gp120-A/E (gp120-A/E-cons)
(SEQ ID NO: 10)
LWVTVYYGVPVWRDADTTLFCASDAKAHETEVHNVWATHACVPTDPNPQEIHLENVTENFNMWKNNMVEQM

QEDVISLWDQSLKPCVKLTPLCVTLNCTNANLTNNNINGSNIIGNITDEVRNCSFNMTTELRDKKQKVHAL

FYKLDIVQIEDNSNSSEYRLINCNTSVIKQACPKISFDPIPIHYCTPAGYAILKCNDKNFNGTGPCKNVSS

VQCTHGIKPVVSTQLLLNGSLAEEEIIIRSENLTNNAKTIIVHLNKSVEINCTRPSNNTRTSITIGPGQVF

YRTGDIIGDIRKAYCEINGTKWNEVLKQVTGKLKEHFNNKTIIFQPPSSGGDLEITMHHFNCRGEFFYCNTT

KLFNNTCIGNETMEGCNGTIILPCKIKQIINMWQGVGQAMYAPPISGRINCVSNITGILLTRDGGANNTAN

ETFRPGGGNIKDNWRSELYKYKVVQIEPLGIAPTRAKRRVVE

UG21-9
(SEQ ID NO: 11)
LWVTVYYGVPVWKEATTTLFCASDAKSYEAEAHNIWATHACVPTDPNPQEIVLENVTENFNIWKNNMVEQM

HDDIISLWDQSLKPCVKLPPLCVTLNCTEWKNATTNATNEGIGMKNCSFTEVRDKKKQAYALFYKLDVVQM

NDDNSTNTSYRLINCNASTITQACPKISFEPIPIHYCAPAGFAILKCNDKKFNGTGPCKNVSTVQCTHGIK

PVVSTQLLLNGSLAEEEIIIRSENLTNNAKIIIVHLNESVPINCTRPYDKVSYRTPIGVGRASYTTRIKGD

IRQAHCNISGEKWNKTLQQVAAKLRDLLNQTAIIFKPSSGGDPEITTHSFNCGGEFFYCNTSGLFNNSVWT

SNSTIGANGTITLPCRIKQIINMWQGVGKAMYTPPIEGQINCSSTITGLLLTRDGGVKNNSQNETFRPGGG

DMRDNWRNELYKYKVVRIEPLGLAPTKARRRVVE

92US715.6
(SEQ ID NO: 12)
LWVTVYYGVPVWKEANTTLFCASDAKAYDTEVHNVWATHACVPTDPDPQEVELENVTENFNMWKNNMVEQM

HEDIISLWDQSLKPCVKLTPLCVTLNCTNLRNDTNTTRNATNTTSSETMMEEGEIKNCSFNITTSIRDKVQ

KEFALFYKLDVVPIENDTTSYRLISCNTSVLTQACPKVSFEPIPIHFCAPAGFAILKCKDKKFNGTGPCTN

VSTVQCTHGIKPVVSTQLLLNGSLAEEEVVIRSANLSDNAKTIIVQLNESVQMNCTRPNNNTRKSIHIGPG

RAFYTTGETIGDIRQAHCNLSRTKWNETLKRIVIKLREQYENKTIVFNQSSGGDPEIVMLSFNCGGEFFYC

NSTKLFNSTWNGTESNNTGDDPIVLPCRIKQVINMWQEVGKAMYAPPIRGQIRCSSNITGLLLTRDGGNSN

ETNTTEIFRPGGGNMKDNWRSELYKYKVVRIEPLGIAPTRAKRRVVQ

-continued

TH14-12
(SEQ ID NO: 13)
LWVTVYYGVPVWKEATTTLFCASDAKAYDTEVHNVWATHACVPTDPNPQEVVLGNVTENFNMWKNNMVEQM

HEDIISLWDQSLKPCVKLTPLCVTLNCTDLRNATNTSSTMEGGEIKNCSFNITTSIKTKVKDYALFYKLDV

VPIDNDNTSYRLINCNTSVITQACPKVSFEPIPIHYCTPAGFAILQCNNKKFNGTGPCTNVSTVQCTHGIR

PVVSTQLLLNGSLAEEEVVIRSSNFTDNARVIIVQLNESVEINCTRPNNNTRKSIHLGPGRAWYTTGQIIG

DIRQAHCNLSSTKWNNTLRQITEKLREQFGNKTIVFNQSSGGDPEIVMHSFNCGGEFFYCNTTQLFNSTWN

DTSTWNNNTGNGTITLPCRIKQIVNMWQEVGKAMYAPPIRGQIRCSSNITGLLLTRDGGNSENKTTETFRP

GGGDMRDNWRSELYKYKVVKIEPLGVAPTKPKRRVVQ

93MW959
(SEQ ID NO: 14)
LWVTVYYGVPVWKDAKTTLFCASDAKAYEREVHNVWATHACVPTDPNPQEIVWENVTENFNMWKNDIVDQM

HEDIISLWDQSLKPCVKLTPLCVTLNCSNANNTATNNVTATNNVTSDMKNCSFNATTELRDKRQKVYALFY

KLDIVPLNEKDNSSSGEYRLINCSTSTVTQACPKVSFDPIPIHYCTPAGYAILKCNNKTFNGTGPCHNVST

VQCTHGIKPVVSTQLLLNGSLAEGEIIIRSENLTNNVKTIIVHLNESVEIVCTRPNNNTRRSIRIGPGQVF

YANNDIIGDIRQAHCNISKDVWNSTLQKVGKKLKEHFPNKTITFEPHSGGDLEITTHSFNCRGEFFYCNTS

GLFNSNFNDTEGNSTLSITLPCRIKQIINMWQEVGRAMYAPPIEGNITCKSNITGLLLTRGGGPTNTKTET

FRPGGGDMRDNWRSELYKYKVVEIKPLGVAPTKAKRRVVE

Polypeptide compositions can include one, two, or more, e.g., three or more, four or more, or all five polypeptides from the group consisting of the polypeptides encoded by nucleic acid molecules comprising a nucleotide sequence that has at least or about 90%, e.g., at least or about 92%, 95%, 96%, 97%, 98%, 99%, or 100%, identity to the nucleotide sequence of SEQ ID NOs:1, 3, 5, 7, and 9. For example, polypeptide compositions can include or consist of polypeptides encoded by nucleic acid molecules comprising or consisting of a nucleotide sequence that has at least or about 90% identity to the nucleotide sequence of SEQ ID NOs:1 and 3; SEQ ID NOs:1, 3, and 5; SEQ ID NOs:1, 3, 5, and 7; SEQ ID NOs:3, 5, 7, and 9; SEQ ID NOs:5, 7, and 9; SEQ ID NOs:1, 3, 5, and 9; SEQ ID NOs:1, 3, 7, and 9; SEQ ID NOs:1, 5, 7, and 9; SEQ ID NOs:1 and 9; SEQ ID NOs:3 and 9; SEQ ID NOs:5 and 9; or SEQ ID NOs:7 and 9.

The terms "protein" and "polypeptide" both refer to any chain of amino acids, regardless of length or post-translational modification (e.g., glycosylation or phosphorylation). Thus, the terms "Env gps protein," and "Env gps polypeptide," include full-length naturally occurring isolated proteins, as well as recombinantly or synthetically produced polypeptides that correspond to the full-length naturally occurring proteins, or to a fragment of the full-length naturally occurring or synthetic polypeptide.

The term "Env gps polypeptide" includes biologically active fragments of naturally occurring or synthetic Env gps polypeptides. Fragments of a polypeptide can be produced by any of a variety of methods known to those skilled in the art, e.g., recombinantly, by proteolytic digestion, and/or by chemical synthesis. Internal or terminal fragments of a polypeptide can be generated by removing one or more nucleotides from one end (for a terminal fragment) or both ends (for an internal fragment) of a nucleic acid that encodes the polypeptide. Expression of such mutagenized DNA can produce polypeptide fragments. Digestion with "end-nibbling" endonucleases can thus generate DNAs that encode an array of fragments. DNAs that encode fragments of a protein can also be generated, e.g., by random shearing, restriction digestion, chemical synthesis of oligonucleotides, amplification of DNA using the polymerase chain reaction, or a combination of the above-discussed methods. Fragments can also be chemically synthesized using techniques known in the art, e.g., conventional Merrifield solid phase FMOC or t-Boc chemistry. For example, peptides of the present invention can be arbitrarily divided into fragments of desired length with no overlap of the fragments, or divided into overlapping fragments of a desired length.

In the case of polypeptide sequences that are less than 100% identical to a reference sequence, the non-identical positions are preferably, but not necessarily, conservative substitutions for the reference sequence. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Where a particular polypeptide is said to have a specific percent identity to a reference polypeptide of a defined length, the percent identity is relative to the reference polypeptide. Thus, a polypeptide that is 50% identical to a reference polypeptide that is 100 amino acids long can be a 50 amino acid polypeptide that is completely identical to a 50 amino acid long portion of the reference polypeptide. It also might be a 100 amino acid long polypeptide that is 50% identical to the reference polypeptide over its entire length.

For large-scale production of recombinant HIV proteins, transfectant cell lines are generated (e.g., Chinese Hamster Ovary cell transfectants), and cell lines that stably express the HIV proteins are generated from the transfectants. Lines that overexpress the protein are selected for production. Master and working cell banks of selected cells are maintained. Proteins are expressed by growing cells in large-scale cultures in protein-free medium. Supernatants of the cells are harvested. Protein is then purified (e.g., using affinity chromatography, ion exchange chromatography, and/or gel filtration chromatography), and tested for purity. Proteins are purified and concentrated using techniques such as gel filtration and ion exchange chromatography. Next, proteins are evaluated for identity, potency, purity, quantity, sterility, the presence of endotoxin, and general safety according to Good Manufacturing Practice (GMP) guidelines. Identity can be determined with ELISA with antibodies specific for the clade of the protein. Potency can be evaluated with ELISA (e.g., reactivity of rabbit sera with the purified protein). Purity can be evaluated with SDS-PAGE and silver stain analyses of the protein, and size-exclusion high-performance liquid chromatography. Quantities can be determined by Coomassie-based assays, spectrophotometric assays, and volume measurements. The quality of protein preparations can be determined by visual inspection and pH measurements. Sterility can be determined by methods described in 21 C.F.R. 610.12. Endotoxin can be determined by Limulus Amebocyte assays. General safety can be determined by methods described in 21 C.F.R. 610.11.

Polypeptide compositions containing an immunogenically effective amount of a recombinant HIV protein, or fragments thereof, can be administered. Suitable compositions can include, for example, lipopeptides (e.g., Vitiello et al., 1995, J. Clin. Invest. 95:341), peptide compositions encapsulated in poly(DL-lactide-co-glycolide) ("PLG") microspheres (see, e.g., Eldridge et al., 1991, Molec. Immunol., 28:287-94; Alonso et al., 1994, Vaccine, 12:299-306; Jones et al., 1995, Vaccine 13:675-81), and peptide compositions contained in immune stimulating complexes (ISCOMS) (see, e.g., Takahashi et al., 1990, Nature 344: 873-75; Hu et al., 1998, Clin. Exp. Immunol. 113:235-43).

Useful carriers that can be used with the immunogenic compositions and vaccines described herein are well known, and include, for example, thyroglobulin, albumins such as human serum albumin, tetanus toxoid, polyamino acids such as poly L-lysine, poly L-glutamic acid, influenza, hepatitis B virus core protein, and the like. The compositions and vaccines can contain a physiologically tolerable (i.e., acceptable) diluent such as water, or saline, typically phosphate buffered saline. The compositions and vaccines also typically include an adjuvant. Adjuvants such as QS-21, incomplete Freund's adjuvant, aluminum phosphate, aluminum hydroxide, or alum, are examples of materials well known in the art. Additionally, CTL responses can be primed by conjugating S proteins (or fragments, derivative or analogs thereof) to lipids, such as tripalmitoyl-S-glycerylcysteinyl-seryl-serine ($P_3CSS$).

Also within the invention are nucleic acid molecules encoding fusion proteins in which a portion of an Env gps polypeptide is fused to an unrelated polypeptide to create a fusion protein. For example, the polypeptide can be fused to a hexa-histidine tag or a FLAG tag to facilitate purification of bacterially expressed polypeptides or to a hemagglutinin tag or a FLAG tag to facilitate purification of polypeptides expressed in eukaryotic cells. The fusion partner can be, for example, a polypeptide that facilitates secretion, e.g., a secretory sequence. Such a fused polypeptide is typically referred to as a preprotein. The secretory sequence can be cleaved by the host cell to form the mature protein.

Administration of Polypeptide Compositions

Immunization with a composition containing an HIV polypeptide composition, e.g., via injection, aerosol, oral, transdermal, transmucosal, intrapleural, intrathecal, or other suitable routes, induces the immune system of the host to respond to the composition. In one embodiment, an Env protein is administered. In some embodiment, a composition of Env proteins is administered.

An exemplary range for an immunogenic amount of polypeptide composition is 5 µg/kg-500 µg/kg, e.g., 10-100 µg/kg of total protein, with adjuvant. In one embodiment, a dose of 325 µg of a polypeptide composition is administered to a human (18-55 years of age, 45-75 kg). An exemplary program of administration of the polypeptide composition includes a first intramuscular boost 4 weeks after the final nucleic acid immunization, followed by a second intramuscular boost with the polypeptide composition 4 weeks after the first boost. Alternatively, the polypeptide composition can be administered before or at the same time as a nucleic acid immunization or without a nucleic acid immunization.

Kits

Kits comprising the nucleic acid and polypeptide compositions are provided. The kits can include one or more other elements including: instructions for use; other reagents, e.g., a diluent, devices or other materials for preparing the composition for administration; pharmaceutically acceptable carriers; and devices or other materials for administration to a subject. Instructions for use can include instructions for therapeutic application (e.g., DNA vaccination and protein boosting) including suggested dosages and/or modes of administration, e.g., in a human subject, as described herein.

The kit can further contain at least one additional reagent, such as a diagnostic or therapeutic agent, e.g., a diagnostic agent to monitor an immune response to the compositions in the subject, or an additional therapeutic agent as described herein (see, e.g., "Combination Therapies," below).

In one embodiment, the kit includes a vial (or other suitable container) containing nucleic acids encoding two, three, four, five, or six distinct HIV Env gps. The kit also includes a second vial containing recombinant HIV Env gps that are the same Env gps as encoded by the nucleic acids in the kit. The kit can include QS-21 adjuvant (50 µg/dose/subject) and cyclodextrin as an excipient (30 mg/subject). The adjuvant and the excipient are formulated with the protein, and can be included in the formulation or packaged separately within the kit.

Combination Therapies

The nucleic acid and polypeptide compositions described herein can be used in methods of treating subjects at risk for being infected with HIV, subjects infected with HIV, and subjects suspected to be infected with HIV. It is well within the skills of an ordinary practitioner to recognize a subject that has, or is at risk of developing, an HIV infection.

The methods of treating these subjects with these compositions can include combination therapies, in which other HIV treatments are administered. For example, a subject undergoing DNA vaccination with protein boosting can be administered anti-retroviral drugs individually, or as Highly Active Antiretroviral Therapy ("HAART"), which refers to therapy with various combinations of nucleoside reverse transcriptase inhibitors, non-nucleoside reverse transcriptase inhibitors, and HIV protease inhibitors.

Nucleoside reverse transcriptase inhibitors include, e.g., zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS- 180194); and Iodenosine (FddA), 9-(2,3-dideoxy-2-fluoro-b-D-threo-pentofuranosyl)adenine.

Non-nucleoside reverse transcriptase inhibitors include nevirapine (BI-RG-587); delaviradine (BHAP, U-90152); and efavirenz (DMP-266).

Protease inhibitors include saquinavir (Ro 31-8959); ritonavir (ABT-538); indinavir (MK-639); nelfnavir (AG-1343) available under the VIRACEPT™ trade name from Agouron Pharmaceuticals, Inc.; amprenavir (141W94), a non-peptide protease inhibitor, tradename AGENERASE™; and lasinavir (BMS-234475).

The subjects can also be those undergoing any of a variety of anti-retroviral therapy treatments. Thus, for example, subjects can be those being treated with one or more of an entry inhibitor (e.g., enfuvirtide (FUZEON®)), a CCR5 receptor antagonist (e.g., maraviroc (SELZENTRY®)), a reverse-transcriptase inhibitor (e.g., zidovudine (RETROVIR®), a protease inhibitor (e.g., atazanavir (REYATAZ®), darunavir (PREZISTA®), fosamprenavir (LEXIVA®), and ritonavir (NORVIR®)), an integrase inhibitor (e.g., Raltegravir (ISENTRESS®)), and a maturation inhibitor (e.g., Bevirimat, Vivecon). The new nucleic acid and polypeptide compositions described herein can enhance the effectiveness of any known AIDS therapies, e.g., by reducing the HIV viral load in the infected patient. The compositions and methods described herein can be used as an adjunct therapy to enhance an infected individual's immune response against the virus.

Evaluating Immune Responses to Vaccinations and Protein Boosts

Advances in the field of immunology have allowed more thorough and sensitive evaluations of cellular responses to candidate HIV vaccines. Such assays as intracellular staining (e.g., flow cytometry) and ELISPOT (an enzyme-linked immunosorbent assay format), allow detecting and counting cells producing cytokines (e.g., TNFα and IFN-γ) in response to antigens. For example, isolation of splenocytes or peripheral blood monocyte cells (PBMCs) from animals or human patients followed by in vitro challenge with HIV epitope such as V3, and finally testing by ELISPOT and/or intracellular cytokine staining (ICS), can determine the potential for a cell-mediated immune response in vaccine recipients. Flow cytometry using tetramers (i.e., molecules consisting of four copies of a given class I molecule bound to their cognate peptide and alkaline phosphatase) allows the enumeration of antigen-specific T cells (e.g., detection of T cells that recognize specific peptides bound to major histocompatibility complex (MHC) class I molecules). A standard chromium release assay can be used to assess cytotoxicity. To assess a cell-mediated immune response to a DNA vaccine, the more traditional approaches of measuring T cell proliferation in response to antigen and CTL-mediated killing of autologous cells expressing HIV epitopes can also be used.

ELISA assays and Western blots can be used to assess humoral immune responses. In particular, ELISA and Western blots can be used to assess antibody binding, antibody neutralizing capability, antibody-mediated fusion inhibition, and antibody-dependent cytotoxicity.

EXAMPLES

The invention is further described in the following examples, which do not limit the scope of the invention described in the claims.

Example 1: Creation of Consensus A/E gp120 Sequence

Since no gp120 DNA vaccines from subtype A/E from the initial screen were able to elicit NAb against more than 50% of the viruses tested, and the numbers of available wild-type E gp120 antigens are limited, a subtype A/E consensus gp120 immunogen (gp120-A/E-cons) was designed based on the available A/E Env sequences from Genbank. Available HIV-1 clade A/E complete Env protein sequences in the HIV database as of October 2009 were used, and those protein sequences were aligned to create a consensus gp120 sequence using computer software DS-Gene. Because of sequence diversity, the computer software could not identify a consensus sequence in some of constant regions and most of the variable regions of gp120. Accordingly, those regions were designed based on known neutralizing epitopes and most frequent length range of variable regions published in literature. The final artificial gp120-A/E-cons protein (SEQ ID NO:10) had good antigenicity when expressed by an in vitro mammalian cell system, as shown by recognition of well-known neutralizing antibodies, such as 2G12 (targeting glycan epitope), b12 (targeting CD4 binding site), and PG9 (targeting V2 quaternary epitope). In an immunogenicity study, gp120-A/E-cons could induce broad NAb responses as shown in Table 4.

Example 2: gp120 Gene Codon-Optimization

Codon usage of gp120 genes from HIV-1 were analyzed with MacVector 7.2 software against codon preference of *Homo sapiens*. The less optimal codons in gp120 genes were changed to specifically selected codons in mammalian systems to promote higher expression of the gp120 proteins. Codon-optimization was performed not only to change codons for mammalian protein expression, but also performed to make mRNA more stable and the gene more favorable for transcriptional and translational processes. During sequence optimization, the following cis-acting sequence motifs were avoided: internal TATA-boxes, chi-sites and ribosomal entry sites; AT-rich or GC-rich sequence stretches; ARE, INS, and CRS sequence elements; cryptic splice donor and acceptor sites; and branch points. Despite such DNA level sequence changes, the final codon-optimized gp120 gene sequences still produced the same gp120 amino acid sequences as in the original HIV-1 viruses. The codon-optimized gp120 genes were chemically synthesized by Geneart (Regensburg, Germany) and individually cloned into DNA vaccine vectors or CHO cell expression vectors downstream of a CMV promoter, and with a tissue plasminogen activator (tPA) leader sequence, to express the gp120 protein in mammalian cells.

```
CMV Promoter
                                              SEQ ID NO: 15)
AATATTGGCTATTGGCCATTGCATACGTTGTATCTATATCATAATATGTA

CATTTATATTGGCTCATGTCCAATATGACCGCCATGTTGACATTAGTTAT

TGACTAGTTATTAATAGTAATCAATTACGGGGTCATTAGTTCATAGCCCA

TATATGGAGTTCCGCGTTACATAACTTACGGTAAATGGCCCGCCTGGCTG

ACCGCCCAACGACCCCCGCCCATTGACGTCAATAATGACGTATGTTCCCA

TAGTAACGCCAATAGGGACTTTCCATTGACGTCAATGGGTGGAGTATTTA

CGGTAAACTGCCCACTTGGCAGTACATCAAGTGTATCATATGCCAAGTCC
```

-continued

```
GCCCCCTATTGACGTCAATGACGGTAAATGGCCCGCCTGGCATTATGCCC

AGTACATGACCTTACGGGACTTTCCTACTTGGCAGTACATCTACGTATTA

GTCATCGCTATTACCATGGTGATGCGGTTTTGGCAGTACACCAATGGGCG

TGGATAGCGGTTTGACTCACGGGGATTTCCAAGTCTCCACCCCATTGACG

TCAATGGGAGTTTGTTTTGGCACCAAAATCAACGGGACTTTCCAAAATGT

CGTAATAACCCCGCCCCGTTGACGCAAATGGGCGGTAGGCGTGTACGGTG

GGAGGTCTATATAAGCAGAGCTCGTTTAGTGAACCGTCAGATCGCCTGGA

GACGCCATCCACGCTGTTTTGACCTCCATAGAAGACACCGGGACCGATCC

AGCCTCCGCGGCCGGGAACGGTGCATTGGAACGCGGATTCCCCGTGCCAA

GAGTGACGTAAGTACCGCCTATAGACTCTATAGGCACACCCCTTTGGCTC

TTATGCATGCTATACTGTTTTTGGCTTGGGGCCTATACACCCCCGCTCCT

TATGCTATAGGTGATGGTATAGCTTAGCCTATAGGTGTGGGTTATTGACC

ATTATTGACCACTCCCCTATTGGTGACGATACTTTCCATTACTAATCCAT

AACATGGCTCTTTGCCACAACTATCTCTATTGGCTATATGCCAATACTCT

GTCCTTCAGAGACTGACACGGACTCTGTATTTTTACAGGATGGGGTCCCA

TTTATTATTTACAAATTCACATATACAACAACGCCGTCCCCCGTGCCCGC

AGTTTTTATTAAACATAGCGTGGGATCTCCACGCGAATCTCGGGTACGTG

TTCCGGACATGGGCTCTTCTCCGGTAGCGGCGGAGCTTCCACATCCGAGC

CCTGGTCCCATGCCTCCAGCGGCTCATGGTCGCTCGGCAGCTCCTTGCTC

CTAACAGTGGAGGCCAGACTTAGGCACAGCACAATGCCCACCACCACCAG

TGTGCCGCACAAGGCCGTGGCGGTAGGGTATGTGTCTGAAAATGAGCTCG

GAGATTGGGCTCGCACCGCTGACGCAGATGGAAGACTTAAGGCAGCGGCA

GAAGAAGATGCAGGCAGCTGAGTTGTTGTATTCTGATAAGAGTCAGAGGT

AACTCCCGTTGCGGTGCTGTTAACGGTGGAGGGCAGTGTAGTCTGAGCAG

TACTCGTTGCTGCCGCGCGCGCCACCAGACATAATAGCTGACAGACTAAC

AGACTGTTCCTTTCCATGGGTCTTTT tPA Leader
                                           (SEQ ID NO: 16)
ATGGATGCAATGAAGAGAGGGCTCTGCTGTGTGCTGCTGCTGTGTGGAGC

AGTCTTCGTTTCG
```

Example 3: Expression and Purification of gp120

Synthetic, codon-optimized gp120 nucleic acid molecules comprising nucleotide sequences of SEQ ID NOs:1, 3, 5, 7, or 9 were expressed in CHO cells and purified with $ZnCl_2$ to precipitate non-glycosylated proteins, as described by Kolbe (U.S. Pat. No. 5,276,141), which is incorporated herein by reference in its entirety. Cells were harvested from three liters of fed-batch spinner flask and three liters of SUB. As shown in FIGS. 1A and 1B, $ZnCl_2$ treatment reduced a great number of co-eluting contaminants in SEC fractions. Treatment with $ZnCl_2$ also removed most unrelated proteins, as shown in a non-reduced PAGE analysis (FIG. 2), and contaminating enzymes such as fucosidase (FIG. 3).

Example 4: Construction of HIV-1 Envelope Glycoproteins Gp120 DNA Vaccines from Clade A, B, C, D, and A/E Primary Isolates Previously published data demonstrated that a cocktail of three to five Env immunogens is effective in eliciting protective antibodies (where neutralizing antibody was used as a biomarker) against HIV-1 isolates from different subtypes in both animal and human pilot studies (Wang et al., *Virology* 350, 34-47, 2006; Wang et al., *Vaccine* 26:3947-3957, 2008). Those pilot studies were done when there were only limited numbers of molecular clones of primary HIV-1 Env antigens available. Since then, more molecular clones and their gene sequences have become available, which enables an investigation to determine whether all primary HIV-1 Env gps have the same levels of immunogencity in eliciting a protective immune response and whether improved formulations can be developed with better selected Env immunogens to elicit a protective immune response with antibodies of higher potency and/or expanded breadth.

The immunogenicity of 62 HIV-1 Env immunogens was screened and only a small percentage of them were more effective than others in eliciting a broad neutralizing antibody response. Further, a new 5-valent Env formulation with immunogens selected from this screening study is more effective than a previously reported "DP6-001" 5-valent formulation in eliciting more potent and broad neutralizing antibodies (Wang et al., *Vaccine* 26:3947-3957, 2008).

Because there is no information on the relationship between the biological features of any Env from a primary HIV-1 virus and its immunogenicity, 62 Env immunogens were collected from viruses with very different biological phenotypes in the current studies. This set of 62 Env immunogens was collected from a wide range of sources including from different infected tissues (e.g., blood, lymph node, and brain), and from 16 countries in Africa, South America, North America, Europe, and Asia covering different HIV-1 subtypes or clades (e.g., A, B, C, D, E or A/E, F, and G).

A New Zealand White (NZW) rabbit model was used in this study as previous studies demonstrate that rabbits are highly immunogenic and provide a large volume of serum to allow a wide range of assays (Vaine et al., *Vaccine* 28:2999-3007, 2010). A DNA prime-protein boost immunization approach was used as it can be more effective than either DNA alone or protein alone to elicit high quality antibody responses (Vaine et al., *Vaccine* 28:2999-3007, 2010; Vaine et al., *PLoS ONE* 5:e13916, 2010; Wang et al., *Vaccine* 26:3626-3633, 2008; Suguitan et al., *PLoS ONE* 6:e21942, 2011). In this example, each Env immunogen in the form of gp120 was used as a DNA prime immunization and a fixed set of five recombinant gp120 proteins as shown in Table 1 was used as the boost.

TABLE 1

Five gp120 proteins used for protein boost

| gp120 protein | Clade | Origin | SEQ ID NO: |
|---|---|---|---|
| UG21-9 | A | Uganda | 11 |
| 92US715.6 | B | USA | 12 |
| JR-FL | B | USA | 4 |
| TH14.12 | B | Thailand | 13 |
| 93MW959 | C | Malawi | 14 |

Rabbits first received three DNA immunizations (one gp120-expressing DNA plasmid at 36 ug per immunization by a gene gun) at Weeks 0, 2, and 4, followed by 4 weeks rest, and then were boosted twice with recombinant gp120 proteins (10 ug per gp120 protein for a total of 50 ug per immunization) at Weeks 8 and 12 delivered by IM injection mixed with incomplete Freund's adjuvant (IFA).

The rationale of using a fixed 5-valent gp120 mix as the boost was based on the following reasons: 1) it can focus on the effect of DNA priming step, which tests the difference of immunogenicity of candidate gp120 immunogens; 2) preliminary studies have shown DNA priming is the most critical step in determining the specificity of NAb response in a DNA prime-protein boost approach.

At the end of study, neutralization antibody (NAb) assays were conducted. The rabbit immune sera were tested for NAb against a panel of 13 pseudotyped viruses expressing a wide range of primary Env: five from clade B and two each from clades A, C, D, and E (Table 2). Three sensitive or TCLA viruses are included as the controls (Table 2). Either pre-bleed or empty DNA vector immunized rabbit sera are included as negative controls.

TABLE 2

Sixteen HIV-1 pseudotyped viruses used in neutralization assays

| | Clade | Virus |
|---|---|---|
| Clade B Sensitive viruses | | MN |
| | | NL43 |
| | | SF162 |
| Primary Env pseudotyped viruses from various clade | Clade A | 92RW020 |
| | | 94UG103 |
| | Clade B | AC10.0.29 |
| | | PVO.4 |
| | | QH0692.42 |
| | | SC422661.8 |
| | | JRCSF |
| | Clade C | 93IN905 |
| | | 98CN006 |
| | Clade D | 92UG046 |
| | | 94UG114 |
| | Clade E | 92TH021 |
| | | CMU02 |

Based on the breadth of neutralizing antibody activities, gp120 DNA immunogens could be divided into three groups: broad (11/62, 17.7%), which neutralized>50% of viruses in this testing panel; intermediate (11/62, 17.7%), which neutralized 25-50% viruses; and narrow (40/62, 64.5%), which neutralized<25% of the viruses (Table 3).

TABLE 3

Breadth of NAb responses induced by priming with individual gp120-expressing DNA vaccines, followed with the boost of a fixed, 5-valent gp120 protein boosts against 16 pseudotyped viruses

| Sub-type | Envelope | Tissue of Isolation | Origin | No. of PV neutralized | % of PV neutralized |
|---|---|---|---|---|---|
| A | 92RW020.5 | PBMC | Rwanda | 1 | 6% |
| A | CA1 | PBMC | Camaroon | 2 | 13% |
| A | 92UG037.1 | PBMC | Uganda | 7 | 44% |
| C | 92BR025.9 | PBMC | Brazil | 2 | 13% |
| C | 96ZM651.2 | PBMC | Zambia | 2 | 13% |
| C | Du123-56 | PBMC | S. Africa | 2 | 13% |
| C | ZM153 | PBMC | Zambia | 2 | 13% |
| C | ZM233 | PBMC | Zambia | 2 | 13% |
| C | ZM53 | PBMC | Zambia | 2 | 13% |
| C | 96BW01B22 | PBMC | Botswana | 3 | 19% |
| C | 96BW15C02 | PBMC | Botswana | 3 | 19% |
| C | Cap210 | Plasma | S. Africa | 3 | 19% |
| C | Du156-12 | PBMC | S. Africa | 3 | 19% |
| C | DU422 | PBMC | S. Africa | 3 | 19% |
| C | ZM109 | PBMC | Zambia | 3 | 19% |
| C | ZM197 | PBMC | Zambia | 3 | 19% |
| C | ZM214 | Plasma | Zambia | 3 | 19% |
| C | ZM249 | Plasma | Zambia | 3 | 19% |
| C | CAP45 | Plasma | S. Africa | 4 | 25% |
| C | DU172 | PBMC | S. Africa | 4 | 25% |
| C | 93MW965.26 | PBMC | Malawi | 15 | 94% |
| D | 92UG021.16 | PBMC | Uganda | 14 | 88% |
| A/E | 93TH976.1 | PBMC | Thailand | 2 | 13% |
| A/E | Consensu | | | 5 of 8 | 63% |
| F1 | 93BR020.17 | PBMC | Brazil | 7 | 44% |
| G | 93UG975.10 | PBMC | Uganda | 3 | 19% |
| B | WIT04561 | Brain | USA | 1 | 6% |
| B | 515.01 | PBMC | Trinidad | 2 | 13% |
| B | P6B-42 | Lymph Node | UK | 2 | 13% |
| B | PV0-04 | Plasma | USA | 2 | 13% |
| B | REJ4541 | Plasma | USA | 2 | 13% |
| B | THR04156 | Plasma | USA | 2 | 13% |
| B | TRJ04551 | PBMC | Italy | 2 | 13% |
| B | TR0.11 | Plasma | USA | 2 | 13% |
| B | 692.42 | PBMC | Trinidad | 3 | 19% |
| B | 1168.01 | PBMC | us | 3 | 19% |
| B | ADA (ADB) | Brain | USA | 3 | 19% |
| B | Ba-L | Plasma | USA | 3 | 19% |
| B | H78639 | Brain | USA | 3 | 19% |
| B | PSB-12 | Lymph node | UK | 3 | 19% |
| B | P6B33 | Brain | UK | 3 | 19% |
| B | P6LN-85 | PBMC | Italy | 3 | 19% |
| B | Yu-2 | Brain | USA | 3 | 19% |
| B | AC10.0.29 | PBMC | us | 4 | 25% |
| B | ADA | PBMC | USA | 4 | 25% |
| B | 89.6 | PBMC | USA | 5 | 31% |
| B | CAAN5352 | PBMC | USA | 5 | 31% |
| B | RHPA4259 | Plasma | Trinidad | 5 | 31% |
| B | SC422661.8 | PBMC | USA | 5 | 31% |
| B | SF162 | Plasma | USA | 5 | 31% |
| B | 1196.01 | PBMC | US | 6 | 38% |
| B | 5768.04 | PBMC | US | 6 | 38% |
| B | P6LN40 | Lymph node | UK | 6 | 38% |
| B | 93US715.6 | PBMC | USA | 8 | 50% |
| B | AC10.44 | PBMC | UK | 9 | 56% |
| B | P5LN-27 | Lymph Node | UK | 9 | 56% |
| B | 6535 | PBMC | USA | 10 | 63% |
| B | 93-20#59 | Brain | UK | 11 | 69% |
| B | 6101LN | PBMC | USA | 12 | 75% |
| B | 93-176#93 | Brain | UK | 13 | 81% |
| B | 92-353#27 | Brain | UK | 14 | 88% |
| *B | JR-FL | Brain | UK | 14 | 88% |

*Indicates the Env immunogens included in the new poly-valent vaccine formulation.

Example 5: New 5-Valent gp120 Vaccine Formulation

Based on the gp120 immunogen screening results, one of the best gp120 immunogens that could be induce broad NAb responses from each of the five major circulating HIV-1 subtypes A, B, C, D and E (A/E), was selected to form a new 5-valent gp120 vaccine formulation, as show in Table 4.

TABLE 4

New 5-valent gp120 Immunogens

| Envelope | Subtype | Tissue of Isolation | Origin | % of PV neutralized | Nucleotide SEQ ID NO | Polypeptide SEQ ID NO |
|---|---|---|---|---|---|---|
| 92UG037.1 | A | PBMC | Uganda | 44% | 1 | 2 |
| JR-FL | B | Brain | UK | 88% | 3 | 4 |
| 93MW965.26 | C | PBMC | Malawi | 94% | 5 | 6 |
| 92UG021.16 | D | PBMC | Uganda | 88% | 7 | 8 |
| gp120-AE-cons | A/E | N/A | N/A | 63% | 9 | 10 |

A second rabbit immunogenicity study was conducted to compare the relative immunogenicity between the original 5-valent DP6-001 gp120 formulation that was tested in previously reported Phase I clinical study and the new 5-valent gp120 formulation shown in Table 4.

In this study, DNA sequence encoding each of these five gp120 immunogens were codon-optimized (SEQ ID NOs:1, 3, 5, 7, and 9). At the same time, recombinant gp120 proteins were produced from each of these five gp120 genes in a mammalian expression system (SEQ ID NOs:2, 4, 6, 8, and 10) and used as the boost gp120 protein vaccines.

Figure 4:
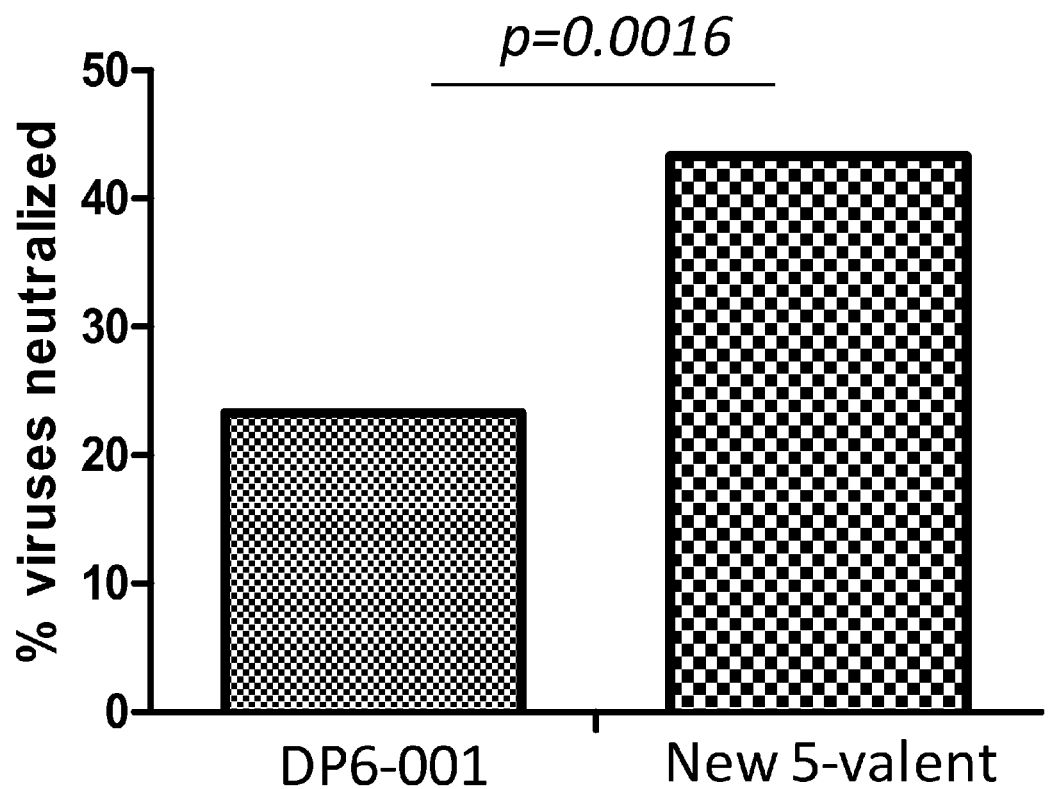
FIG. 4 is a bar graph depicting percent of HIV-1 pseudoviruses neutralized by rabbit sera immunized with a DP6-001 vaccine formulation compared to the new 5-valent gp120 formulation described herein. The p value (p=0.0016) indicates a significant difference in neutralization breadth between DP6-001 and the new 5-valent vaccine groups.
Figure 5:
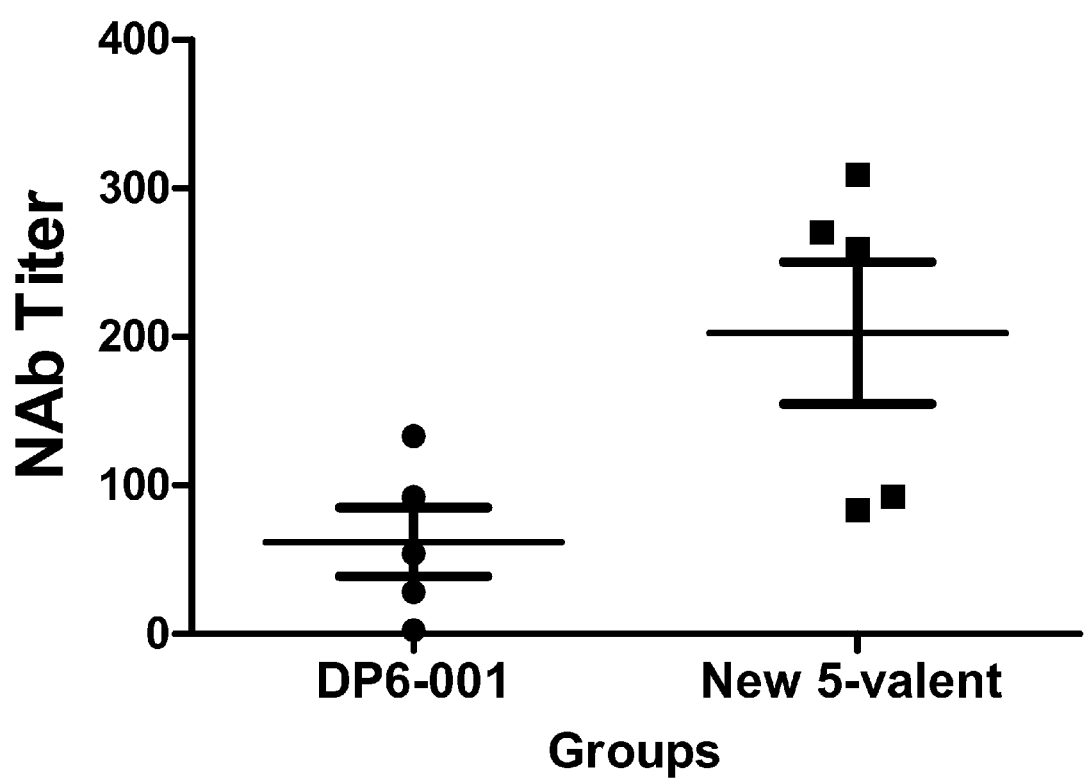
FIG. 5 is a graph comparing neutralizing antibody titers from rabbit sera immunized with the DP6-001 formulation compared to the new 5-valent gp120 formulation against a sample of pseudovirus SS1196.

Rabbits received a DNA prime at weeks 0, 2, and 4 and protein boosts at weeks 8 and 12 with either the new 5-valent gp120 formulation or the DP6-001 gp120 formulation. The rabbit serum samples were collected to evaluate the gp120-specific antibody responses and neutralizing antibody responses. The results demonstrated that at two weeks after the final protein immunization, the new 5-valent gp120 vaccine formulation elicited NAb responses with significantly improved breadth (FIG. 4) against a panel of 22 pseudoviruses from clade B and C (Table 5) and potency (FIG. 5) compared to the DP6-001 gp120 vaccine formulation.

TABLE 5

A panel of clade B and C pseudoviruses

| Clade B | Clade C |
|---|---|
| SS1196.1 | ZM249.PL1 |
| PVO.4 | ZM197M.PB7 |
| QH0692.42 | Du156.12 #1 |
| AC10.0.29 | Du172.17 #3 |
| SC 422661.8 | ZM135M.PL10a |
| REJO4541.67 | CAP45.2.00.G3 |
| 6535.3 | Du422.1 |
| CAAN5342.A2 | ZM53M.PB12 |
| TRJO4551.58 | ZM214.pB7 |
| RHPA4259.7 | ZM109F.PB4 |
| WITO4160.3 | CAP210.2.00.E8 |

For a given polyvalent vaccine, any combination of the two or more of the components listed in Table 4 can be used. The polyvalent vaccine can be administered as naked DNA plasmid, with a facilitating agent, with an adjuvant, and/or with a protein boost described herein.

Example 6: Immune Response Induced by HIV-1 Primary Isolate DNA Vaccine

DNA Immunization.

A female New Zealand Rabbit (2 kg) received three monthly DNA immunizations by gene gun. Each shot delivered 1 µg of DNA and a total of 36 non-overlapping shots were delivered to each rabbit at each of the three time points at the surface of shaved abdominal skin after animals were anesthetized according to IACUC approved protocols. The serum samples were collected immediately before, and 4 weeks after each immunization.

ELISA (Enzyme-Linked Immunosorbent Assay).

Rabbit sera samples were tested for gp120-specific IgG antibody responses by ELISA. Microtiter plates were coated with ConA (5 µg per well) for 1 hour and then washed 5 times with washing buffer (PBS at pH 7.2 with 0.1% Triton X-100). Env antigens at 1 µg/ml were added (100 µl for each well) and incubated for 1 hour at room temperature. Blocking was done with 200 µl/well of 4% milk-whey blocking buffer for 1 hour at room temperature. After removal of the blocking buffer and another 5 time washes, 100 µl of serially diluted sera were added and incubated for 1 hour. The plates were washed 5 times and incubated with 100 µl of biotinylated anti-rabbit IgG diluted at 1:1000 for 1 hour followed with washes. Then, horseradish peroxidase-conjugated streptavidin diluted at 1:2000 was added (100 µl/well) and incubated for 1 hour. After the final washes, 100 µl of fresh TMB substrate was added per well and incubated for 3.5 min. The reaction was stopped by adding 25 µl of 2 M $H_2SO_4$, and the optical density (OD) of the plate was measured at 450 nm. ELISA assays in which sera reactivity to gp120 was evaluated are described.

Western Blot Analysis.

The gp120 antigens transiently expressed from 293T-cell supernatants and cell lysates were subjected to denaturing SDS-PAGE and blotted onto polyvinylidene fluoride (PVDF) membrane. Blocking was done with 0.1% I-Block. Rabbit serum immunized with mixed polyvalent gp120 DNA vaccines was used as the detecting antibody at 1:500 dilution and incubated for 45 minutes. Subsequently, the membranes were washed with blocking buffer and then reacted with AP-conjugated goat anti-rabbit or human IgG at 1:5000 dilution. After final wash, Western-light substrate was applied to the membranes for 5 minutes. Once the membranes were dry, Kodak films were exposed to the membrane and developed with an X-Omat processor. Env reactivity was also observed by Western blot.

Example 7: Neutralization Assay

One way of determining the potential efficacy of a vaccine in animals is to perform in vitro functional assays of the animal's immune sera and cells. The HIV-1 pseudovirus neutralization assays described below are examples of evaluating humoral responses in vaccinated test animals in vitro. The presence of neutralizing antibodies in the serum of a vaccinated animal can be tested in a functional assay referred to as a neutralization assay.

Pseudovirus Neutralization Assay in TZM-B1 Cells:

This type of neutralization assay is based on reductions in luciferase (Luc) reporter gene expression after a single round of virus infection with pseudotyped HIV-1 viruses in TZM-b1 cells (Montefiori DC. Evaluating neutralizing antibodies against HIV, SW and SHIV in luciferase reporter gene assays. In: Coligan J E, A. M. Kruisbeek, D. H. Margulies, E. M. Shevach, W. Strober, and R. Coico, eds., editor. *Current Protocols in Immunology*: John Wiley & Sons, 2004: 12.1.1-.1.5). Each pseudotyped HIV-1 virus expresses a HIV-1 primary Env glycoprotein. Neutralizing antibody levels in immune rabbit sera were measured against a panel of pseudotyped viruses (Table 5). In this assay, 200 TCID$_{50}$ of virus was incubated with serial dilutions of heat-inactivated rabbit serum samples in triplicate in a total volume of 150 µl for 1 h at 37° C. in 96-well flat-bottom culture plates. Freshly trypsinized cells (10,000 cells in 100 µl of growth medium containing 75 µg/ml DEAE dextran) were added to each well. One set of control wells received cells plus virus (virus control) and another set received cells only (background control). After 48 h incubation, 100 µl of cells was transferred to a 96-well black solid plate (Costar) for measurements of luminescence using Bright Glo substrate solution, as described by the supplier (Promega). The percent neutralization was calculated by comparing experimental wells to virus control wells. Neutralization titer was the dilution at which RLUs were reduced by 50% compared to virus control wells after subtraction of background RLUs using pre-bleed sera.

PhenoSense Neutralization Assay:

This type neutralization assays is used recombinant virus pseudotyped with HIV-1 primary envelope protein and a firefly luciferase indicator gene (Richman et al., Proc Natl Acad Sci USA 100:4144-9, 2003). The pseudoviruses (Table 2) were incubated for 1 hour at 37° C. with serial dilutions of heat-inactivated rabbit sera. U87 cells that express CD4 plus the CCR5 and CXCR4 co receptors were inoculated with virus dilutions in the absence of added cations. Virus infectivity was determined 3 days later by measuring the amount of luciferase activity expressed in infected cells. Neutralizing activity was calculated as the percent inhibition of viral replication (luciferase activity) at each antibody dilution compared with an antibody-negative control: % inhibition={1−[luciferase+Ab/luciferase−Ab]}×100. Titers were presented as the reciprocal of the plasma dilution conferring 50% inhibition (IC50) (Richman et al., Proc Natl Acad Sci USA 100:4144-9, 2003). The specificity control was composed of a virus pseudotyped with an aMuLV envelope. An HIV-serum combination was considered to have positive neutralization if the inhibition of HIV was at least 50% and >3× higher IC50 than the same plasmas tested with aMuLV while the prebleed was not scored positive. The starting sera dilution used in the neutralization assays was 1:20.

Example 8: Phase I Clinical Study of New 5-Valent Vaccine

Human clinical trials are conducted for the purpose of determining safety of a vaccine and for determining efficacy of a vaccine. To determine safety, normal volunteers are immunized with the vaccine. The incidence of side effects is noted. To determine efficacy, NIH established protocols are followed. High-risk population (e.g., drug users, populations with high-risk sexual activity, populations in which the incidence of HIV is high). To test a high risk population, the incidence of HIV infection in the negative control group who are immunized with a DNA vaccine containing the vector alone is compared to the incidence of HIV infection in the test group receiving the polyvalent DNA vaccine containing primary isolate sequences (e.g., sequences of gp120). A double blind trial is conducted. The immunization regimen is, for example, three DNA vaccine immunizations by gene gun, each administered a month apart. Sera are drawn during the regimen to monitor immune status by experiments such as described in Example 4, above. Additionally, cell-mediated immunity (CTL response) is tested in human patients by isolating PBMCs followed by in vitro functional testing of these cells as described above. The presence of neutralizing antibodies in the patient's sera is then tested as described above. Infection by HIV is tested and statistical analysis is done to determine if the incidence is significantly different between control and test groups.

A phase I clinical study to assess the new 5-valent gp120 formulation is conducted as follows. The objectives of the study are to assess the safety of multiple dosing levels of the new 5-valent gp120 formulation, to assess the ability of the new 5-valent gp120 formulation to induce humoral immune responses to vaccine components, and to assess the ability of the new 5-valent gp120 formulation to induce cell-mediated immune responses.

Approximately 36 human subjects participate in the study. These subjects are healthy, HIV-uninfected adult volunteers of 18-55 years of age. They are at low or minimal risk for HIV infection as defined by HVTN Risk Status. They have no history of previous experimental HIV vaccine inoculations.

Each participant receives one of three dose regimes in which the new 5-valent gp120 formulation is administered via ID or IM routes. Administration is randomized, with a rising DNA component, multiple doses, with a follow-on protein vaccine boost. One test program of administration to humans is as follows: administer approximately 50 µg/kg of the new 5-valent gp120 formulation DNA composition at week 0, week 4, and week 12, (i.e., 3 doses per person, approx. 2.5 mg dose for a person of 50 kg); and administer 7 µg/kg of the new 5-valent gp120 formulation polypeptide composition at week 20 and week 28.

To assess the ability of the new 5-valent gp120 formulation to induce humoral responses to vaccine components, ELISA is performed using a pool of the gp120 glycoproteins used for vaccination. ELISA using HIV-1 Czm Gag protein is also performed. Neutralizing antibody assays against panels of laboratory adapted and primary HIV-1 isolates are performed by HVTN-certified laboratories. Additional solid-phase assays such as Western blots can be used to further confirm immunity and characterize immune responses and distinguish between vaccination and potential new infection. For example, if the vaccine does not include gp41, the vaccinated subject would not exhibit a response to gp41. Detection of gp41-reactivity in the subject would then be indicative of potential new infection.

To assess the ability of the new 5-valent gp120 formulation to induce cell-mediated immune responses, IFN-γ ELISPOT assays specific for HIV-1 Gag or Env epitopes can be performed. Bulk culture cytotoxic T-cell assays and flow cytometric intracellular cytokine staining assays can also be used.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of inducing an immune response against human immunodeficiency virus (HIV) or an HIV epitope in a subject, the method comprising administering to the subject at least one of the following:
   a nucleic acid composition comprising at least two different synthetic, codon-optimized nucleic acid molecules comprising a nucleotide sequence that has at least 90% identity to the nucleotide sequence of at least two of SEQ ID NO:1, 3, 5, 7, and 9, wherein one of the synthetic, codon-optimized nucleic acid molecules comprises a nucleotide sequence that has at least 90% identity to the nucleotide sequence of SEQ ID NO:5 or 7; and
   a polypeptide composition comprising at least two different isolated polypeptides encoded by a synthetic, codon-optimized nucleic acid molecule comprising a nucleotide sequence that has at least 90% identity to the nucleotide sequence of at least two of SEQ ID NO:1, 3, 5, 7, and 9, wherein one of the synthetic, codon-optimized nucleic acid molecules comprises a nucleotide sequence that has at least 90% identity to the nucleotide sequence of SEQ ID NO:5 or 7;
   wherein the nucleic acid composition and/or the polypeptide composition are administered in an amount sufficient to induce an immune response against HIV or an HIV epitope in the subject.

2. The method of claim 1, wherein the nucleic acid composition is administered before the polypeptide composition.

3. The method of claim 1, wherein the nucleic acid composition is administered three times before the polypeptide composition is administered two times.

4. The method of claim 1, wherein the polypeptide composition is administered before the nucleic acid composition.

5. The method of claim 1, wherein the nucleic acid composition is administered at the same time as the polypeptide composition.

6. The method of claim 1, wherein a neutralizing humoral immune response is induced.

7. The method of claim 1, wherein a cell-mediated immune response is induced.

8. The method of claim 1, wherein the subject is human.

9. The method of claim 1, wherein the method further comprises administering a therapeutic agent for HIV infection.

10. The method of claim 9, wherein the therapeutic agent for HIV infection is a nucleoside reverse transcriptase inhibitor, a non-nucleoside reverse transcriptase inhibitor, or an HIV protease inhibitor.

11. The method of claim 1, wherein the synthetic, codon-optimized nucleic acid molecule comprises a nucleotide sequence that has at least 92% identity to the nucleotide sequence of SEQ ID NO:5 or 7.

12. The method of claim 1, wherein the synthetic, codon-optimized nucleic acid molecule comprises a nucleotide sequence that has at least 95% identity to the nucleotide sequence of SEQ ID NO:5 or 7.

13. The method of claim 1, wherein the synthetic, codon-optimized nucleic acid molecule comprises a nucleotide sequence that has at least 97% identity to the nucleotide sequence of SEQ ID NO:5 or 7.

14. The method of claim 1, wherein the synthetic, codon-optimized nucleic acid molecule comprises a nucleotide sequence that has at least 99% identity to the nucleotide sequence of SEQ ID NO:5 or 7.

15. The method of claim 1, wherein the method comprises administering to the subject at least one of the following:
   a nucleic acid composition comprising at least two different synthetic, codon-optimized nucleic acid molecules comprising a nucleotide sequence that has at least 90% identity to the nucleotide sequence of at least two of SEQ ID NO:1, 3, 5, 7, and 9, wherein one of the synthetic, codon-optimized nucleic acid molecules comprises a nucleotide sequence that has at least 90% identity to the nucleotide sequence of SEQ ID NO:5; and
   a polypeptide composition comprising at least two different isolated polypeptides encoded by a synthetic, codon-optimized nucleic acid molecule comprising a nucleotide sequence that has at least 90% identity to the nucleotide sequence of at least two of SEQ ID NO:1, 3, 5, 7, and 9, wherein one of the synthetic, codon-optimized nucleic acid molecules comprises a nucleotide sequence that has at least 90% identity to the nucleotide sequence of SEQ ID NO:5.

16. The method of claim 1, wherein the method comprises administering to the subject at least one of the following:
   a nucleic acid composition comprising at least three different synthetic, codon-optimized nucleic acid molecules comprising a nucleotide sequence that has at least 90% identity to the nucleotide sequence of at least two of SEQ ID NO:1, 3, 5, 7, and 9, wherein one of the synthetic, codon-optimized nucleic acid molecules comprises a nucleotide sequence that has at least 90% identity to the nucleotide sequence of SEQ ID NO:5; and
   a polypeptide composition comprising at least three different isolated polypeptides encoded by a synthetic, codon-optimized nucleic acid molecule comprising a nucleotide sequence that has at least 90% identity to the nucleotide sequence of at least three of SEQ ID NO:1, 3, 5, 7, and 9, wherein one of the synthetic, codon-optimized nucleic acid molecules comprises a nucleotide sequence that has at least 90% identity to the nucleotide sequence of SEQ ID NO:5.

17. The method of claim 1, wherein the method comprises administering to the subject at least one of the following:
   a nucleic acid composition comprising at least four different synthetic, codon-optimized nucleic acid molecules comprising a nucleotide sequence that has at least 90% identity to the nucleotide sequence of SEQ ID NO:1, 3, 5, 7, and 9, wherein one of the synthetic, codon-optimized nucleic acid molecules comprises a nucleotide sequence that has at least 90% identity to the nucleotide sequence of SEQ ID NO:5; and
   a polypeptide composition comprising at least four different isolated polypeptides encoded by a synthetic, codon-optimized nucleic acid molecule comprising a nucleotide sequence that has at least 90% identity to the nucleotide sequence of SEQ ID NO:1, 3, 5, 7, and 9, wherein one of the synthetic, codon-optimized nucleic acid molecules comprises a nucleotide sequence that has at least 90% identity to the nucleotide sequence of SEQ ID NO:5.

18. The method of claim 1, wherein the method comprises administering to the subject at least one of the following:
   a nucleic acid composition comprising at least two different synthetic, codon-optimized nucleic acid molecules comprising a nucleotide sequence that has at least 90% identity to the nucleotide sequence of at least two of SEQ ID NO:1, 3, 5, 7, and 9, wherein one of the synthetic, codon-optimized nucleic acid molecules comprises a nucleotide sequence that has at least 90% identity to the nucleotide sequence of SEQ ID NO:7; and a polypeptide composition comprising at least two different isolated polypeptides encoded by a synthetic, codon-optimized nucleic acid molecule comprising a nucleotide sequence that has at least 90% identity to the nucleotide sequence of at least two of SEQ ID NO:1, 3, 5, 7, and 9, wherein one of the synthetic, codon-optimized nucleic acid molecules comprises a nucleotide sequence that has at least 90% identity to the nucleotide sequence of SEQ ID NO:7.

19. The method of claim 1, wherein the method comprises administering to the subject at least one of the following:

a nucleic acid composition comprising at least three different synthetic, codon-optimized nucleic acid molecules comprising a nucleotide sequence that has at least 90% identity to the nucleotide sequence of at least two of SEQ ID NO:1, 3, 5, 7, and 9, wherein one of the synthetic, codon-optimized nucleic acid molecules comprises a nucleotide sequence that has at least 90% identity to the nucleotide sequence of SEQ ID NO:7; and a polypeptide composition comprising at least three different isolated polypeptides encoded by a synthetic, codon-optimized nucleic acid molecule comprising a nucleotide sequence that has at least 90% identity to the nucleotide sequence of at least three of SEQ ID NO:1, 3, 5, 7, and 9, wherein one of the synthetic, codon-optimized nucleic acid molecules comprises a nucleotide sequence that has at least 90% identity to the nucleotide sequence of SEQ ID NO:7.

20. The method of claim 1, wherein the method comprises administering to the subject at least one of the following:

a nucleic acid composition comprising at least four different synthetic, codon-optimized nucleic acid molecules comprising a nucleotide sequence that has at least 90% identity to the nucleotide sequence of SEQ ID NO:1, 3, 5, 7, and 9, wherein one of the synthetic, codon-optimized nucleic acid molecules comprises a nucleotide sequence that has at least 90% identity to the nucleotide sequence of SEQ ID NO:7; and a polypeptide composition comprising at least four different isolated polypeptides encoded by a synthetic, codon-optimized nucleic acid molecule comprising a nucleotide sequence that has at least 90% identity to the nucleotide sequence of SEQ ID NO:1, 3, 5, 7, and 9, wherein one of the synthetic, codon-optimized nucleic acid molecules comprises a nucleotide sequence that has at least 90% identity to the nucleotide sequence of SEQ ID NO:7.

21. The method of claim 1, wherein the method comprises administering to the subject at least one of the following:

a nucleic acid composition comprising at least two different synthetic, codon-optimized nucleic acid molecules comprising a nucleotide sequence that has at least 90% identity to the nucleotide sequence of at least two of SEQ ID NO:1, 3, 5, 7, and 9, wherein two of the synthetic, codon-optimized nucleic acid molecules comprise a nucleotide sequence that has at least 90% identity to the nucleotide sequence of SEQ ID NO:5 and a nucleotide sequence that has at least 90% identity to the nucleotide sequence of SEQ ID NO:7; and a polypeptide composition comprising at least two different isolated polypeptides encoded by a synthetic, codon-optimized nucleic acid molecule comprising a nucleotide sequence that has at least 90% identity to the nucleotide sequence of at least two of SEQ ID NO:1, 3, 5, 7, and 9, wherein two of the synthetic, codon-optimized nucleic acid molecules comprise a nucleotide sequence that has at least 90% identity to the nucleotide sequence of SEQ ID NO:5 and a nucleotide sequence that has at least 90% identity to the nucleotide sequence of SEQ ID NO:7.

* * * * *

UNITED STATES PATENT AND TRADEMARK OFFICE
CERTIFICATE OF CORRECTION

PATENT NO. : 9,675,687 B2  Page 1 of 1
APPLICATION NO. : 14/776682
DATED : June 13, 2017
INVENTOR(S) : Shan Lu and Shixia Wang It is certified that error appears in the above-identified patent and that said Letters Patent is hereby corrected as shown below:

In the Specification

Column 1, Line 12, delete "which is" and insert --are--.

Columns 21-22, approximately Lines 47-55, please replace the paragraph beginning with "gp-120-B..." with the following paragraph:
--gp120-B (JR-FL)
(SEQ ID NO : 4)
VEKLWVTVYYGVPVWKEATTTLFCASDAKAYDTEVHNVWATHACVPTDPNPQEVVLENVT
EHFNMWKNNMVEQMQEDIISLWDQSLKPCVKLTPLCVTLNCKDVNATNTTNDSEGTMERG
EIKNCSFNITTSIRDEVQKEYALFYKLDVVPIDNNNTSYRLISCDTSVITQACPKISFEPIPIHYCA
PAGFAILKCNDKTFNGKGPCKNVSTVQCTHGIRPVVSTQLLLNGSLAEEEVVIRSDNFTNNAK
TIIVQLKESVEINCTRPNNNTRKSIHIGPGRAFYTTGEIIGDIRQAHCNISRAKWNDTLKQIVIKL
REQFENKTIVFNHSSGGDPEIVMHSFNCGGEFFYCNSTQLFNSTWNNNTEGSNNTEGNTITLPC
RIKQIINMWQEVGKAMYAPPIRGQIRCSSNITGLLLTRDGGINENGTEIFRPGGGDMRDNWRS
ELYKYKVVKIEPLGVAPTKAKRRVVQREKRAV--.

Columns 23-24, approximately Lines 2-10, please replace the paragraph beginning with "gp-120-C..." with the following paragraph:
--gp120-C ((93MW965.26)
(SEQ ID NO : 6)
LWVTVYYGVPVWKEAKTTLFCASEAKAYEKEVHNVWATHACVPTDPNPQEMVLENVTENF
NMWKNDMVNQMHEDIISLWDQSLKPCVKLTPLCVTLNCTNANGTNNNGTVNVNDTMYGEI
KNCSFNMTTELRDKKKQVYALFYKLDIVSLNENSNNSSEYRLINCNTSVITQACPKVTFDPIPI
HYCAPAGYAILKCNNKTFTGIGPCKNVSTVQCTHGIKPVVSTQLLLNGSLAEEEIIVRSENLTD
NVKTIIVHLNESVEIVCTRPNNNTRKSVRIGPGQTFYATGAIIGDIRQAHCNISTIKWNKTLQGV
EKKLKEHFPNKTIEFKPSSGGDLEITTHSFNCRGEFFCCNTSNLFTSNLFTDNLTNTTNITLPCRI
KQIINMWQGVGRAMYAPPIAGNITCKSNITGLLLTRDGGENNRTETFRPGGGDMKDNWRSEL
YKYKVVEIKPLGVAPTGAKRRVVE--.

Signed and Sealed this
Second Day of July, 2019

Andrei Iancu
*Director of the United States Patent and Trademark Office*